United States Patent
Hashiba et al.

(10) Patent No.: US 9,717,477 B2
(45) Date of Patent: Aug. 1, 2017

(54) ULTRASONIC DIAGNOSIS DEVICE AND ULTRASONIC IMAGE ACQUISITION METHOD

(71) Applicant: HITACHI ALOKA MEDICAL, LTD., Tokyo (JP)

(72) Inventors: Kunio Hashiba, Tokyo (JP); Hiroshi Kuribara, Tokyo (JP); Chizue Ishihara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 341 days.

(21) Appl. No.: 14/412,739

(22) PCT Filed: Jun. 24, 2013

(86) PCT No.: PCT/JP2013/067253
§ 371 (c)(1),
(2) Date: Jan. 5, 2015

(87) PCT Pub. No.: WO2014/007100
PCT Pub. Date: Jan. 9, 2014

(65) Prior Publication Data
US 2015/0148678 A1    May 28, 2015

(30) Foreign Application Priority Data
Jul. 5, 2012   (JP) .................. 2012-151189

(51) Int. Cl.
*A61B 8/00* (2006.01)
*G01S 7/52* (2006.01)
(Continued)

(52) U.S. Cl.
CPC ............ *A61B 8/4494* (2013.01); *A61B 8/145* (2013.01); *A61B 8/5207* (2013.01); *A61B 8/56* (2013.01);
(Continued)

(58) Field of Classification Search
CPC .............. G01S 7/5202; G01S 15/8959; G01S 7/52038; G01S 15/8927; G01S 15/8963;
(Continued)

(56) References Cited

U.S. PATENT DOCUMENTS

| 5,577,505 A | 11/1996 | Brock-Fisher et al. |
| 5,678,553 A | 10/1997 | Uhlendorf et al. |

(Continued)

FOREIGN PATENT DOCUMENTS

| JP | 4-146736 A | 5/1992 |
| JP | 2009-22462 A | 2/2009 |

(Continued)

OTHER PUBLICATIONS

International Preliminary Report of Patentability for PCT/JP2013/067253, dated Jan. 15, 2015.

*Primary Examiner* — Bo J Peng
(74) *Attorney, Agent, or Firm* — Baker Botts L.L.P.

(57) ABSTRACT

Provided is a technique that implements harmonic imaging in an ultrasound diagnostic apparatus, being unaffected by the voltage-dependent distortion and nonlinear characteristics of the transmit system in the ultrasound diagnostic apparatus that incorporates the transmit amplifier, the ultrasound probe, and the like, facilitating adjustment of the transmit voltage, and achieving a frame rate substantially equivalent to that of the conventional PI method. In the amplitude modulation method that synthesizes the transmit acoustic fields, thereby eliminating a basic wave component of an acoustic wave and creating an image from nonlinear component echoes being extracted, one transmit and receive out of plural transmits and receptions to obtain one scanning line also serves as the transmit and receive for obtaining other scanning line. The echo signals obtained by the shared transmit and receive are used to form the receive beams respectively on both the scanning lines that share the transmit and receive.

12 Claims, 15 Drawing Sheets

(51) Int. Cl.
  *G01S 15/89* (2006.01)
  *A61B 8/14* (2006.01)
  *A61B 8/08* (2006.01)

(52) U.S. Cl.
  CPC ........ *G01S 7/5202* (2013.01); *G01S 7/52038* (2013.01); *G01S 15/8918* (2013.01); *G01S 15/8927* (2013.01); *G01S 15/8959* (2013.01); *G01S 15/8963* (2013.01); *A61B 8/54* (2013.01)

(58) Field of Classification Search
  CPC ....... G01S 15/8918; A61B 8/56; A61B 8/145; A61B 8/4494; A61B 8/5207; A61B 8/54
  See application file for complete search history.

(56) References Cited

U.S. PATENT DOCUMENTS

| | | | |
|---|---|---|---|
| 6,095,980 A | 8/2000 | Burns et al. | |
| 6,544,184 B1 * | 4/2003 | Guracar | A61B 8/481 600/437 |
| 2009/0024031 A1 | 1/2009 | Ohuchi et al. | |

FOREIGN PATENT DOCUMENTS

| | | |
|---|---|---|
| JP | 2010-51375 A | 3/2010 |
| WO | 2005/059591 A1 | 6/2005 |

* cited by examiner

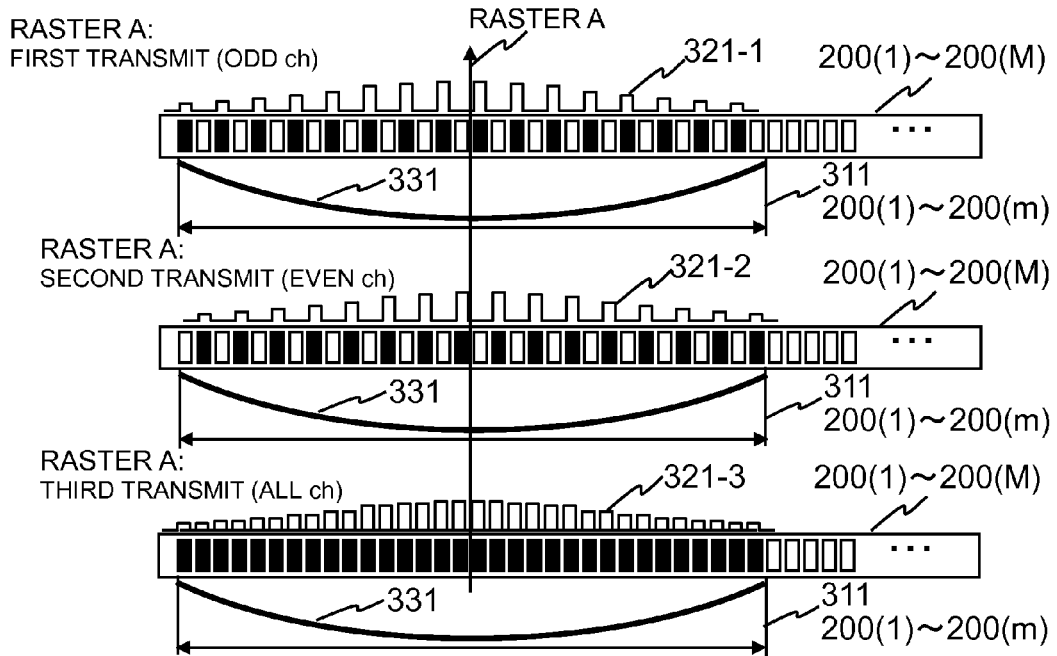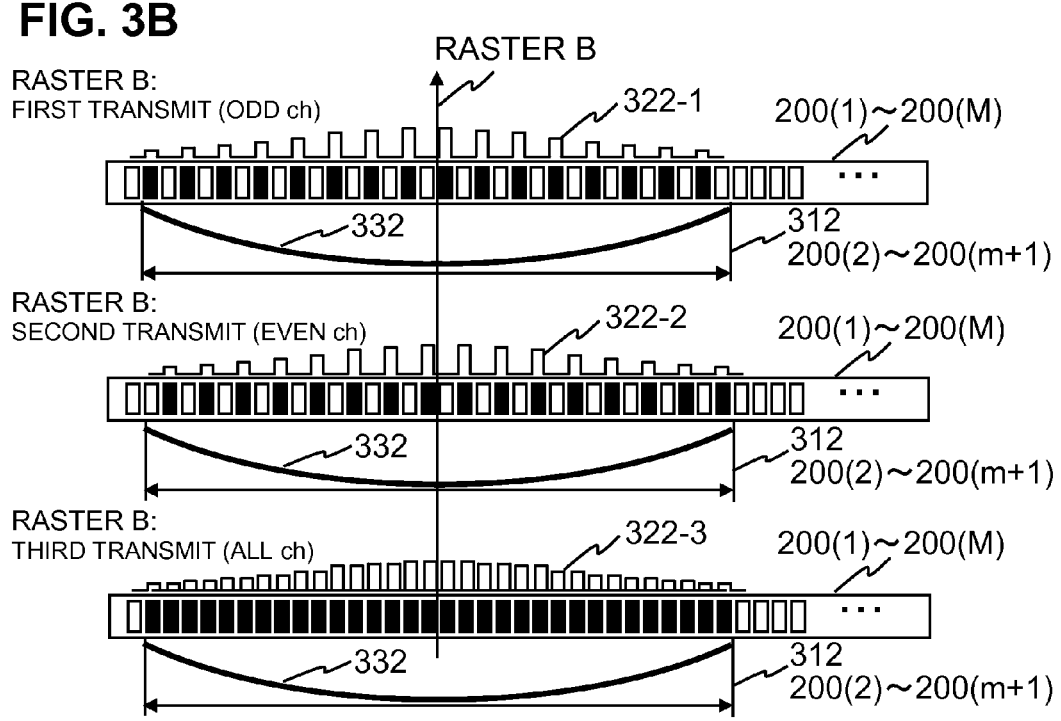

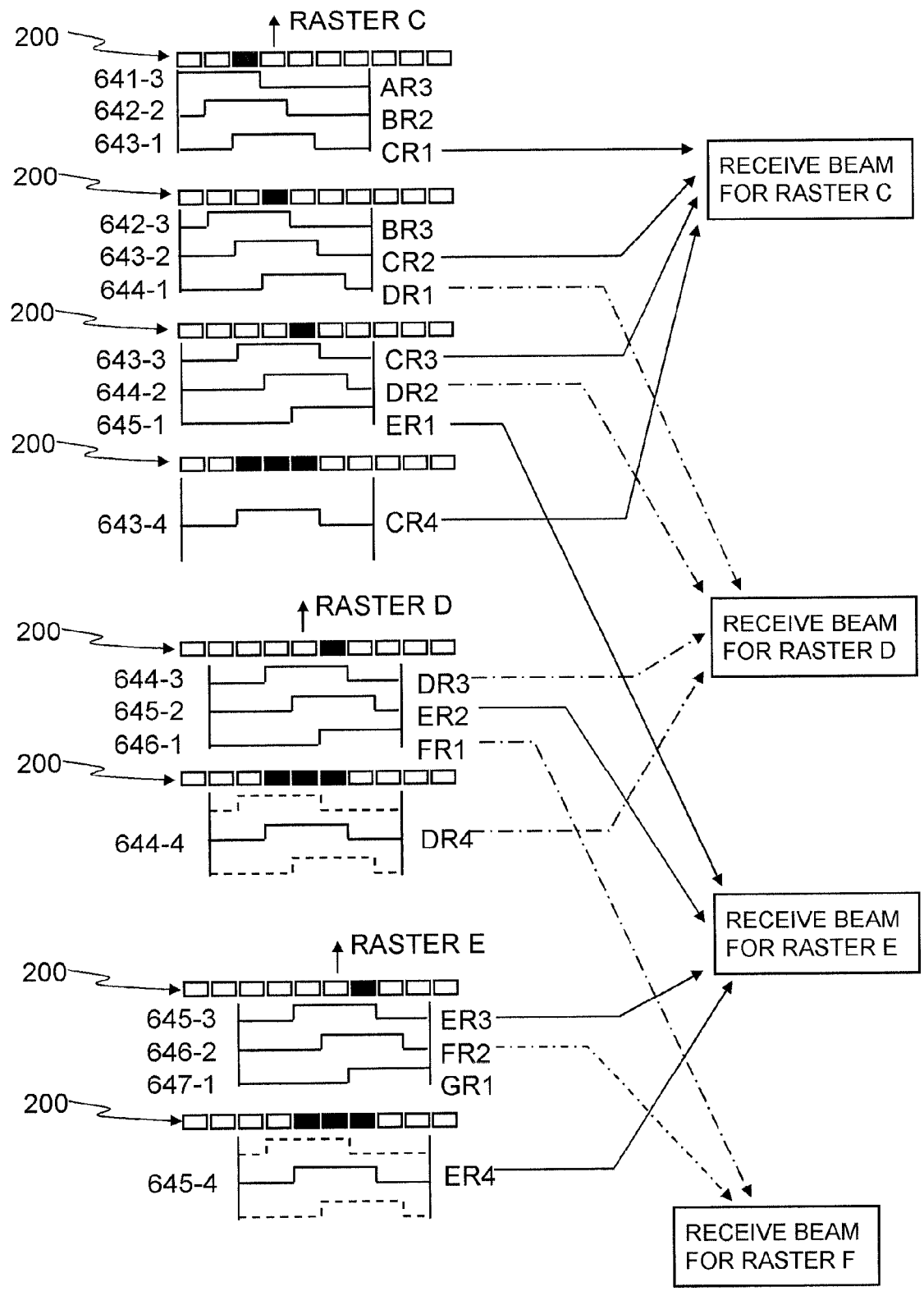

ULTRASONIC DIAGNOSIS DEVICE AND ULTRASONIC IMAGE ACQUISITION METHOD

TECHNICAL FIELD

The present invention relates to an ultrasound imaging technique that performs nonlinear imaging, and more particularly, it relates to a tissue harmonic imaging that utilizes acoustic nonlinear characteristics of a living body, and/or contrast harmonic imaging that utilizes nonlinear oscillation characteristics of a contrast agent.

BACKGROUND ART

The ultrasound diagnostic apparatus transmits ultrasound pulses from an ultrasound probe to the inside of a living body, receives ultrasound echoes scattered or reflected within the body via the ultrasound probe, and applies various signal processes to thus received ultrasound echoes (received echoes), thereby obtaining a ultrasound B-mode image and a blood flow image, and this apparatus is widely used for medical diagnosis.

Waveforms of the ultrasound waves applied to the living body are distorted along with propagation. This is because acoustic waveforms have acoustic nonlinearity, that is, the waveforms proceed rapidly in a portion with high sound pressure, whereas it proceeds slowly in a portion with low sound pressure. This waveform distortion accumulates along with the propagation of acoustic waves. Occurrence of the waveform distortion indicates occurrence of a higher harmonic component or a low-frequency harmonic component assuming the transmitted acoustic wave as a fundamental wave component, in other words, indicating occurrence of a nonlinear component. This nonlinear component occurs in a broadband, in proportion to approximately the square of sound pressure amplitude. Therefore, by creating an image from the nonlinear component, it is possible to obtain an image that excels in contrast resolution and spatial resolution. This type of imaging method is generally referred to as THI (tissue harmonic imaging).

As one method of imaging by the ultrasound diagnostic apparatus, there is an ultrasound contrast imaging method that uses an ultrasound contrast agent. The ultrasound contrast imaging method intravenously injects into a living body, a preparation obtained by stabilizing micro bubbles in micron order size as the ultrasound contrast agent, and then performs ultrasound imaging. This method is widely used for diagnosing disease that is reflected on blood vascular system, such as malignant tumor and infarction. This microbubble type ultrasound contrast agent shows an extremely strong nonlinear response to a few MHz ultrasound wave that is mainly used in ultrasound diagnosis. Therefore, the nonlinear component of the ultrasound echoes in the ultrasound contrast imaging method includes a large amount of ultrasound echoes coming from the ultrasound contrast agent. An imaging method that extracts such ultrasound echoes in the nonlinear component and creates an image therefrom, so as to visualize a vascular structure, and the like, is generally referred to as CHI (contrast harmonic imaging).

As described above, in the THI or the CHI (if it is not necessary to make a distinction therebetween, they are collectively referred to as "harmonic imaging"), an image is created by using the acoustic nonlinear characteristics of acoustic wave propagation through a living body, or the nonlinear component generated on the basis of the nonlinear characteristics in the oscillation of contrast agent. In the ultrasound echo, there exist a fundamental wave component included originally in the transmitted acoustic wave and the aforementioned nonlinear component in a mixed manner, and therefore, it is necessary to extract the nonlinear components from the received echoes. As the method for extracting the nonlinear component from the ultrasound echoes, there are a method for separating the nonlinear component by using a filter (e.g., see the patent document 1), PI (pulse inversion) method (e.g., see the patent document 2), and an amplitude modulation method (e.g., see patent document 3).

The PI method transmits two ultrasound pulses respectively having acoustic wave pulses being inverse, positive and negative, to an identical portion of the living body, and sums the reflection echoes therefrom. Since a fundamental wave component behaves linearly, when the transmit pulses being inverse each other are transmitted, the fundamental wave components of the reflection echoes are also inverse each other, and they cancel each other out when they are added together. On the other hand, the nonlinear components are distorted differently depending on whether the sound pressure is positive or negative. Therefore, even though the transmit pulses being inverse each other are transmitted, they do not form waveforms being inverse and they do not cancel each other out when they are added together. Eventually, when the reflection echoes of the transmit pulses being inverse each other are added together, only the nonlinear components remain.

As described in the patent document 3, the amplitude modulation method performs transmit of ultrasound waves twice, similar to the PI method, and as for the pulse in the second transmit, its acoustic waveform is not inverted, but sound pressure level (amplitude) is made lower than the pulse in the first transmit. By way of example, in the second transmit, the sound pressure amplitude of the pulse is made half of the first transmit pulse. Then, the reflection echo of the second transmit pulse is doubled and subtracted from the reflection echo of the first transmit pulse, thereby removing the fundamental wave components within the reflection echoes. When the amplitude modulation method is applied to the THI, the fundamental wave components are canceled out, and only the nonlinear components remain. When the amplitude modulation method is applied to the CHI, it is possible to extract not only the higher harmonic component of the contrast agent origin, but also the nonlinear component dependent on the sound pressure amplitude of the contrast agent origin, enabling an ultrasound contrast image with a high CTR (contrast-to-tissue ratio) to be obtained.

In addition, a harmonic imaging combining the amplitude modulation method and the PI method is also being devised.

On the other hand, in the imaging method using the PI method or the amplitude modulation method, it is necessary to turn the phase of the transmit voltage waveform by 180 degrees so as to invert the sound pressure waveform, or vary the sound pressure amplitude while maintaining the sound pressure waveform. Therefore, if there is any distortion dependent on the voltage amplitude and phase and/or nonlinear characteristics in the transmit system of the ultrasound diagnostic apparatus that incorporates a transmit amplifier, an ultrasound probe, and the like, it is not possible to remove the fundamental wave component sufficiently.

In order to solve this problem, there is a measure to perform the amplitude modulation method in a transmit sound field by synthesizing transmit aperture (e.g., see the patent document 4). An ultrasound probe is provided with channels made up of plural ultrasound transducers. Those channels are assigned in such a manner that plural channels for transmitting a first transmit pulse P1 and plural channels for transmitting a second transmit pulse P2 become mutually different, entirely or partially. Furthermore, the channel for transmitting a third transmit pulse P3 uses both the channel used for transmitting the first transmit pulse P1 and the channel used for transmitting the second transmit pulse P2. With this configuration, the transmit sound field of the third transmit pulse P3 is obtained by linearly combining the transmit sound field of the first transmit pulse P1 and the transmit sound field of the second transmit pulse P2. Therefore, the operation of P3−(P1+P2) may remove a linear fundamental wave component and extracts the nonlinear component.

PRIOR ART DOCUMENT

Patent Document

Patent Document 1
  U.S. Pat. No. 5,678,553 Specification
Patent Document 2
  U.S. Pat. No. 6,095,980 Specification
Patent Document 3
  U.S. Pat. No. 5,577,505 Specification
Patent Document 4
  Japanese Unexamined Patent Application Publication No. 2009-22462

DISCLOSURE OF THE INVENTION

Problem to be Solved by the Invention

As described above, the transmit and receive performed twice for an identical scanning line, are sufficient in an ordinary amplitude modulation method. However, if there are voltage-dependent distortion and/or nonlinear characteristics in the transmit system of the ultrasound diagnostic apparatus incorporating the transmit amplifier, the ultrasound probe, and the like, it is difficult to remove the fundamental wave component with a high degree of precision. It may be possible to obtain a voltage-dependent transfer function of the transmit system in advance so as to perform shaping of a transmit voltage waveform in such a manner as removing the electrical distortion. However, this makes adjustment extremely cumbersome and complicated, and if there is variation in the channels of the ultrasound probe, the effect may be reduced.

On the other hand, as disclosed by the patent document 4, the amplitude modulation method may solve the problems of the distortion and nonlinear characteristics in the transmit system, the method selecting a channel for transmitting the first transmit pulse P1 and a channel for transmitting the second transmit pulse P2 in a mutually exclusive manner, and synthesizing those channels in the transmit sound field, so that the third transmit pulse P3 is obtained by combining the first transmit pulse P1 and the second transmit pulse P2. Furthermore, it is not necessary to adjust the transmit voltage within one channel in every transmit, facilitating the adjustment of the transmit voltage while imaging is performed. However, in this case, the transmit and receive have to be performed at least three times for an identical scanning line. This may lower the frame rate and there is a possibility of causing somewhat slow movement in a moving image.

In addition, if there is remarkable influence of body motion, the fundamental wave component still remains, even though the operation of "P3−(P1+P2)" is performed.

The present invention has been made in view of the problems above, and an object of the present invention is to provide a technique that implements harmonic imaging in an ultrasound diagnostic apparatus, being unaffected by the voltage-dependent distortion and nonlinear characteristics of the transmit system in the ultrasound diagnostic apparatus that incorporates the transmit amplifier, the ultrasound probe, and the like, facilitating adjustment of the transmit voltage, and achieving a frame rate substantially equivalent to that of the conventional PI method.

Means to Solve the Problem

The present invention is directed to an amplitude modulation method that synthesizes transmit sound fields to remove a fundamental wave component of an acoustic wave and creates an image, from echoes of nonlinear components being extracted, and in the amplitude modulation method, at least one transceiving (transmit and receive), out of plural times of transceiving to obtain one scanning line, serves as the transceiving to obtain another scanning line. Echo signals obtained by the shared transceiving, form receive beams respectively on both the scanning lines obtained by sharing the transceiving.

Specifically, the present invention provides an ultrasound diagnostic apparatus configured to transmit ultrasound pulses to a subject from an ultrasound probe provided with plural channels, and obtain an ultrasound image from echo signals being received, including a transmit beamformer configured to set a transmit apodization that defines as transmit channels, more than one transmit channel for transmitting the ultrasound pulses, out of the plural channels, and a transmit focus delays that defines delay time given to the ultrasound pulses transmitted respectively from the transmit channels in every transmit, a receive beamformer configured to generate receive beams from the echo signals received by the plural channels in every transmit, and a signal processor configured to generate a synthetic receive beam on one scanning line, by synthesizing n (n is an integer at least 3) receive beams, and obtain an ultrasound image, wherein the n receive beams that generate the synthetic receive beam on one scanning line are generated respectively from the echo signals obtained by n-times different transmits, and at least one time out of the n-times different transmits is a shared transmit that serves as the transmit for another scanning line that is different from the aforementioned scanning line.

Effect of the Invention

According to the present invention, in implementing harmonic imaging in an ultrasound diagnostic apparatus, it is possible to establish a configuration unaffected by voltage-dependent distortion and nonlinear characteristics of the transmit system in the ultrasound diagnostic apparatus incorporating the transmit amplifier, the ultrasound probe, and the like, facilitating adjustment of the transmit voltage, and achieving a frame rate substantially equivalent to that of the conventional PI method.

BRIEF DESCRIPTION OF DRAWINGS

FIG. 3A illustrates the transmit apodization and the transmit focus delays in every transmit, in an amplitude modulation method using a conventional transmit aperture;

FIG. 3B illustrates the transmit apodization and the transmit focus delays in every transmit, in an amplitude modulation method using a conventional transmit aperture;

FIG. 15 illustrates the receive apodization in every transmit and receive of the third embodiment.

BEST MODE FOR CARRYING OUT THE INVENTION

<First Embodiment>

Hereinafter, the first embodiment to which the present invention is applied will be explained, with reference to the accompanying drawings. In the entire drawings for explaining the preferred embodiments, constituents having the same function are named and labeled the same, and the function shall not be tediously explained.

Figure 1A:
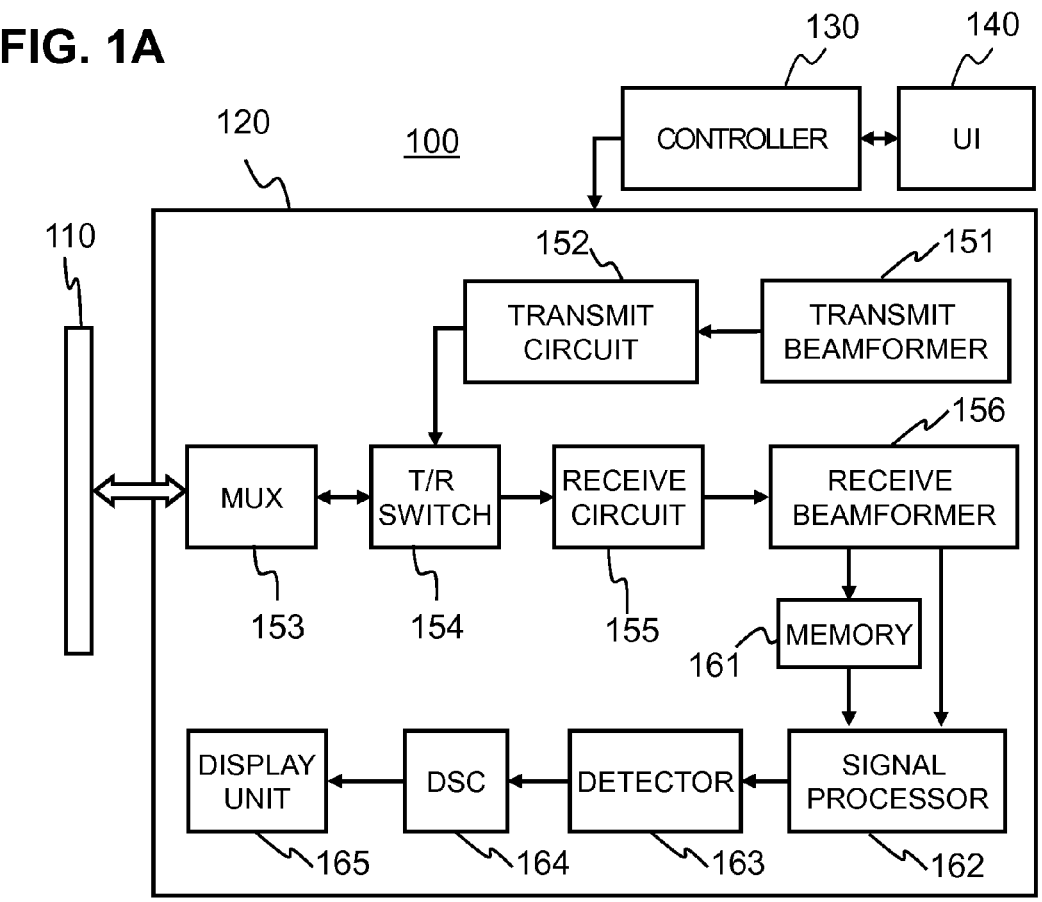
FIG. 1A is a device configuration block diagram illustrating the ultrasound diagnostic apparatus of the first embodiment.

Firstly, with reference to FIG. 1A, the ultrasound diagnostic apparatus 100 of the present embodiment will be explained. The ultrasound diagnostic apparatus 100 of the present embodiment is provided with an ultrasound probe 110, a controller 130, and a controlled unit 120, and a user interface (UI) 140.

The ultrasound probe 110 is provided with more than one electroacoustic conversion element (oscillator) that has a function of conversion, from an electrical signal to an acoustic wave, and from an acoustic wave to an electrical signal. These electroacoustic conversion elements are arranged one-dimensionally or two-dimensionally in a predetermined manner within the ultrasound probe 110, thereby constituting the ultrasound transmit and receive surface. The ultrasound probe 110 is formed in an outer shape being suitable for the use in such a manner as bringing the ultrasound transmit and receive surface into contact with an imaging target (test subject).

Figure 2A:
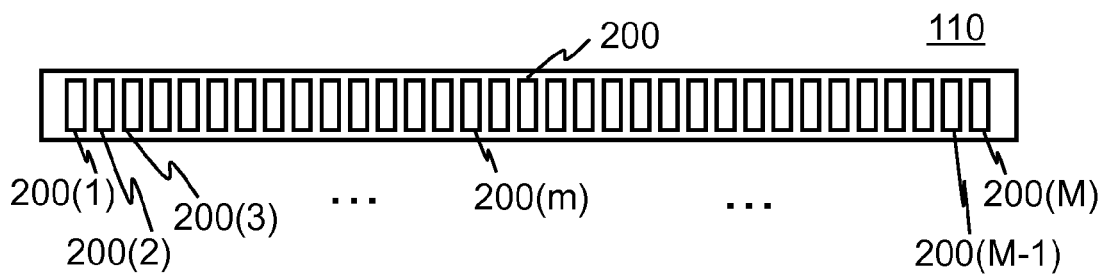
FIG. 2A illustrates a configuration of the channels of the first embodiment.

As illustrated in FIG. 2A, thus arranged plural electroacoustic conversion elements are virtually or physically divided into predetermined plural channels 200. Each channel is made up of at least one electroacoustic conversion element. FIG. 2A illustrates the case where M (M indicates an integer at least one) channels 200 are arranged one-dimensionally. Channel numbers m (m indicates an integer between or equal to 1 to M) are assigned to the individual channels 200, sequentially from either one of ends. When it is necessary to identify each of the channels, each channel is referred to as channel 200($m$).

The controller 130 controls operations of each element in the controlled unit 120. The controller 130 is connected to an UI 140 that accepts an instruction from a user. The controller 130 controls operations of each element in the controlled unit 120 as appropriate according to the instruction accepted from the user via the UI 140, and implements an imaging method such as the THI and CHI, for instance.

The controller 130 is provided with a CPU, a memory, and a storage device. According to the instruction from the user via the UI 140, and the CPU loading programs in the memory and executing them, the programs being held in the storage device in advance, the controls as described above are implemented.

The controlled unit 120 is provided with a transmit beamformer 151 configured to generate a transmit signal that determines a transmit beam, a transmit circuit 152 configured to function as a transmit amplifier that amplifies the transmit signal from the transmit beamformer 151, a cross point switch (MUX) 153 configured to control connection to plural channels 200 serving as a transmit and receive aperture, out of M channels 200, a T/R switch 154 being connected to the ultrasound probe 110, configured to separate a transmit signal from a received signal, thereby separating transmit from reception, a receive circuit 155 being provided with a function of analogue front-end part (AFE) configured to apply amplification and filtering process to the received signal and a function of A/D converter configured to perform analog-digital conversion, a receive beamformer 156 configured to apply a desired filtering process and a delay-and-add process to a received echo signal after the analog-digital conversion, and obtain a receive beam, a memory 161 configured to store the receive beam obtained by the receive beamformer 156, a signal processor 162 configured to use the receive beam stored in the memory 161 and/or the receive beam outputted directly from the receive beamformer 156, perform a linear operation, and obtain a synthetic receive beam, a detector 163 configured to detect the synthetic receive beam, a digital scan converter (DSC) 164 configured to convert the synthetic receive beam after the detection into data for on-screen displays, and a display unit 165 to display the data being converted.

The MUX 153 sets the channel 200 to be connected to the T/R switch 154 in the controlled unit 120, in every transmit and receive. The range of the channels 200 set by the MUX 153 to be connected to the T/R switch are referred to as the transmit and receive aperture 310.

Figure 2B:
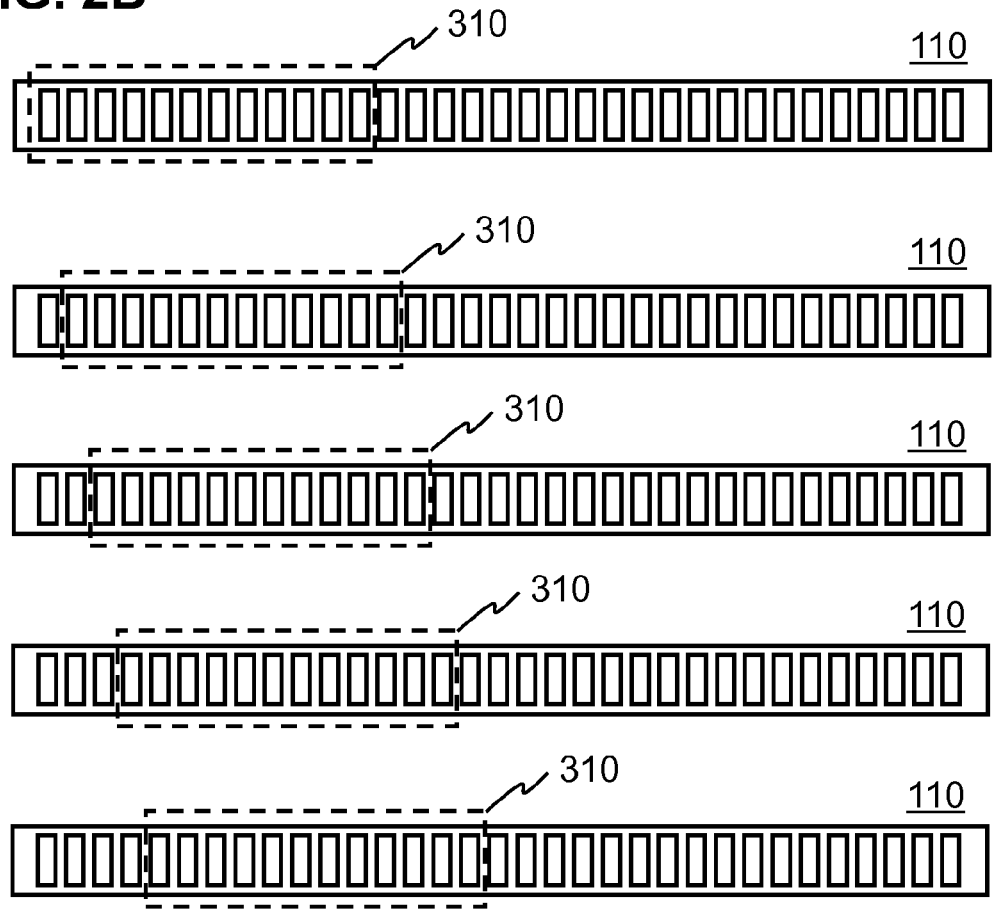
FIG. 2B illustrates the transmit and receive aperture of the first embodiment.

As shown in FIG. 2B, the MUX 153 of the present embodiment changes the channels 200 to be connected in response to transmit and receive, according to the instruction from the controller 130, thereby varying the transmit and receive aperture 310. Variation patterns of the transmit and receive aperture 310 are prepared in advance, and stored in the storage, and the like, provided in the ultrasound diagnostic apparatus 100.

The transmit beamformer 151 is connected to the ultrasound probe 110 via the transmit circuit 152, the T/R switch 154, and the MUX 153. The transmit beamformer 151 of the present embodiment determines voltage to be given to each of the channels 200 of the ultrasound probe 110 and transmits the voltage in the form of a transmit signal to the ultrasound probe 110. In other words, in the present embodiment, control of application voltage by the transmit beamformer 151 determines ultrasound pulses transmitted respectively from the channels 200 of the ultrasound probe 110.

In the present embodiment, the amplitude modulation method synthesizes transmit apertures, thereby removing a fundamental wave component. Therefore, the transmit beamformer 151 of the present embodiment determines information that defines the transmit aperture in every transmit i.e., plural channels for transmitting the ultrasound pulses (hereinafter, referred to as "transmit channels"), and information that defines delay time given to each of the transmit channels so as to decide a focus depth (focal distance) of wave transmit, and generates transmit signals to be sent out to the individual channels 200, according to those determined information items.

In the present embodiment, the information that defines the transmit channels is configured as a transmit apodization. The transmit apodization defines sound pressure of the ultrasound pulses transmitted from the respective channels 200 of the transmit and receive aperture 310. If the sound pressure of the ultrasound pulse transmitted from the respective channels 200 is set to be zero, no ultrasound pulses are transmitted from the channels. This feature is utilized for the transmit beamformer 151 of the present embodiment to set the transmit apodization, and accordingly, selection of the transmit channels is defined simultaneously with defining the sound pressure of the ultrasound pulses transmitted from thus selected transmit channels.

The information defining the delay time to be given to each of the transmit channels is configured as a transmit focus delays. The transmit beamformer 151 controls timing for applying voltage to each of the transmit channels, thereby controlling the delay time given to each of the transmit channels. Generally, the transmit focus delays is determined in such a manner as placing the transmit focal point on the center of a predetermined range. This is referred to as "forming the transmit focus delays with respect to the center position".

As described above, the transmit beamformer 151 of the present embodiment configures settings of the transmit apodization and the transmit focus delays in every transmit. Then, according to thus configured transmit apodization and transmit focus delays, transmit signals to the respective channels 200 being selected by the MUX 153 are generated and outputted to the transmit circuit 152.

It is to be noted that the transmit apodization and the transmit focus delays are configured according to an instruction from a user via the UI 140, or an instruction from the controller 130. The controller 130 stores in the storage device in advance, several types of settings of the transmit apodization and the transmit focus delays for every transmit, and outputs an instruction to the transmit beamformer 151 in response to the user's selection.

Accordingly, under the control of the controller 130, the transmit beamformer 151 outputs transmit signals having the delay time appropriate for the transmit wave focus, as to each of the channels 200, and transfers the transmit signals to electroacoustic elements constituting each of the channels 200 of the ultrasound probe 110, via the transmit circuit 152, the T/R switch 154, and the MUX 153.

Each of the electroacoustic conversion elements in the ultrasound probe 110 converts the transmit signals into the ultrasound pulses. Outputting of the ultrasound pulses from the respective electroacoustic conversion elements forms an acoustic field (transmit beam) that achieves a focus on the position set by the user.

The ultrasound pulses being transmitted are reflected within the imaging target, and echoes being reflected are captured by the ultrasound probe 110, and converted into analog electrical signals in each of the channels 200. The analog electrical signals pass through the MUX 153, the transmit/receive switch (T/R switch) 154, and the receive circuit 155, and then the signals are inputted in the receive beamformer 156 as echo signals.

According to the control of the controller 130, the receive beamformer 156 provides delays to the echo signals as to each of the channels 200, and sums the echo signals, so as to form a receive beam on a predetermined scanning line (raster). Selection of the echo signals to be summed decides the position of the raster being formed. The channels 200 receiving the echo signals to be summed are referred to as "sum channels". When the echo signals are summed, a predetermined delay is given to each of the echo signals, thereby obtaining the receive beam with a desired depth.

The receive beamformer 156 defines the sum channels according to a receive apodization. Delays given to the echo signals obtained in each of the sum channels are defined according to a receive focus delays. The receive beamformer 156 of the present embodiment configures settings of the receive apodization and the receive focus delays in every receiving, and according to the settings, the receive beamformer generates receive beams from a group of echo signals received by the channels 200 defined by the transmit and receive aperture 310.

It is to be noted that the receive beamformer 156 of the present embodiment forms receive beams on plural rasters, from the group of echo signals obtained in each of the channels 200 according to one-time transmit. In order to achieve this, the receive beamformer 156 of the present embodiment is able to configure plural receive apodizations and plural receive focus delays. Various plural receive beams generated from the group of echo signals obtained by one-time transmit are referred to as "receive parallel beams".

In order to generate the receive parallel beams, the receive beamformer 156 of the present embodiment may be provided with plural delay-and-add functions. The delay-and-add function is to give delays to the group of echo signals acquired in the sum channels, according to a predetermined receive focus delays, and add the signals. It is further possible to generate plural beams by time sharing.

As described above, the receive beamformer 156 of the present embodiment configures the receive apodization and the receive focus delays in every receiving, and forms the receive beam on a predetermined raster, according to thus configured receive apodization and the receive focus delays.

The receive apodization and the receive focus delays are set by an instruction from the user via the UI 140 or an instruction from the controller 130. The controller 130 holds in the storage device in advance, several types of settings of the receive apodization and the receive focus delays in every receiving, and outputs an instruction to the receive beamformer 156 in response to the user's selection.

Accordingly, under the control of the controller 130, the receive beamformer 156 outputs the receive beams formed on a predetermined raster, and stores the receive beams in the memory 161. Alternatively, the receive beams are outputted directly to the signal processor 162.

When the signal processor 162 acquires the receive beams the number of which allows one scanning line (raster) to be formed under the control of the controller 130, a linear arithmetic process is performed to generate a synthetic receive beam. Details of this process will be described below. The detector 163 detects the synthetic receive beam being obtained, the DSC 164 converts the synthetic receive beam into data for displays, and the display unit 165 displays the data as an ultrasound diagnosis image.

It is to be noted that the signal processor 162 further applies an amplification process and a predetermined filtering process to the receive beams, in addition to the linear arithmetic process. The amplification process is performed according to TGC (Time gain compensation) and an amplification factor that are set by the user via the UI 140.

It is further possible to configure the transmit beamformer 151, the receive beamformer 156, and the signal processor 162, in such a manner that each of those elements is provided with the CPU and the memory, and each of the above processes are executed when the CPU loads in the memory the programs held in advance. Alternatively, each of the elements may share those resources. Further alternatively, dedicated hardware may constitute each of those elements.

The MUX 153 is not necessarily provided. Byway of example, the T/R switch 154 is connected to all the channels 200, and according to the aforementioned transmit apodization and the receive apodization, a channel to be used for each transmit and receive may be selected. In other words, the transmit beamformer 151 controls the applied voltage to each of the channels 200, thereby setting the channels 200 to be connected. This is effective, for instance, when the number of channels held by the controlled unit 120 of the ultrasound diagnostic apparatus 100 is equal to or larger than the number of channels configured in the ultrasound probe 110.

The configuration of the ultrasound diagnostic apparatus 100, except the ultrasound probe 110, may be mounted on an enclosure as a main unit, separated from the ultrasound probe 110, or a part of this configuration may be provided inside the ultrasound probe 110.

Next, with the use of the aforementioned ultrasound diagnostic apparatus 100, an imaging method that employs the harmonic imaging according to the amplitude modulation method will be explained, the method utilizing synthesis of the transmit apertures. Prior to explaining the imaging method of the present embodiment, a conventional harmonic imaging method according to the amplitude modulation method that utilizes the synthesis of the transmit apertures will be explained with reference to FIG. 3, FIG. 4, and FIG. 5.

In the amplitude modulation method that removes the fundamental wave component by synthesizing the transmit apertures, a waveform of the ultrasound pulse to be synthesized is formed as a transmit sound field, not according to electronic control. Here, an explanation will be made, taking as an example that the signal processor 162 applies operations referred to as harmonic signal processing, to the echo signals obtained by three-time transmits; the first transmit and the second transmit to which the transmit channels are configured in such a manner as mutually exclusive, and the third transmit assuming as the transmit channels, the channels used by both the first transmit and the second transmit, and obtains a synthetic receive beam corresponding to one scanning line.

It is assumed that the ultrasound probe 110 is provided with M channels, the channels from 200(1) to 200(M). In addition, the range of the channels 200 used in the third transmit is assumed as the transmit and receive aperture 310, and the number of the channels of the transmit and receive aperture is assumed as m. Here, m is assumed as even number between or equal to 2 and M.

When an identification number is assigned one by one from the left end of the channels 200 that are used in the third transmit, the channel 200 provided with an odd identification number is referred to as "odd channel", and the channel 200 provided with an even identification number is referred to as "even channel".

FIG. 3A and FIG. 3B illustrate the transmit apodization, transmit focus delays, and the transmit and receive aperture in every transmit for the case above. Here, an explanation will be made taking as one example, the raster A setting the channels from 200(1) to 200($m$) as the transmit and receive aperture 311, and the raster B adjacent to the raster A, setting the channels from 200(2) to 200(m+1) as the transmit and receive aperture 312. In other words, it is assumed that the pitch between the adjacent rasters (e.g., between the raster A and the raster B) corresponds to the unit of the channel 200. In the figure, the black-filled channel 200 represents the transmit channel. The same depiction shall apply hereinafter.

As illustrated in the upper row of FIG. 3A, the transmit apodization 321-1 of the first transmit for the raster A, assuming the channels from 200(1) to 200($m$) as the transmit and receive aperture 311, is configured in such a manner that sound pressure is provided only to the odd channels (odd ch). As illustrated in FIG. 3A, the configured transmit apodization 321-1 is formed in such a manner that the closer is the channel 200 to the raster A, the larger is the sound pressure at which the ultrasound wave is transmitted, for instance. As illustrated in the middle row of FIG. 3A, the transmit apodization 321-2 of the second transmit is configured in such a manner that the sound pressure is provided only to the even channels (even ch). As illustrated in the lower row of FIG. 3A, the transmit apodization 321-3 of the third transmit is configured in such a manner that the sound pressure is provided to all the channels (all ch).

On the other hand, the transmit focus delays 331 is formed for the raster A in any of the transmits. The setting of the transmit focus delays 331 is configured in such a manner that the closer is the channel 200 to the raster A passing through the center of the transmit and receive aperture 311, the larger is the delay time, for instance.

The same shall apply to the transmit for the raster B that is adjacent to the raster A. As illustrated in the upper row of FIG. 3B, the transmit apodization 322-1 of the first transmit for the raster B, assuming the channels from 200(2) to 200(m+1) as the transmit and receive aperture 312, is configured in such a manner that sound pressure is provided only to the odd channels (odd ch). As illustrated in middle row of FIG. 3B, the transmit apodization 322-2 of the second transmit is configured in such a manner that sound pressure is provided only to the even channels (even ch). As illustrated in the lower row of FIG. 3B, the transmit apodization 322-3 of the third transmit is configured in such a manner that sound pressure is provided to all the channels (all ch). On the other hand, the transmit focus delays 332 is formed for the raster B in any of the transmits.

As described above, when the channels from 200($k$) to 200(m+k−1) (k is an integer between or equal to 1 and (M−m)) are set as the transmit and receive aperture 311, control is performed so that only the odd channels (odd ch) of the channels from 200($k$) to 200(m+k−1) are excited in the first transmit. In other words, the ultrasound pulses are controlled to be transmitted only from the odd channels.

Setting the transmit apodization in the transmit beamformer 151 may implement such aforementioned control. In this situation, the transmit focus delays is set to the raster K that is positioned at the center of the channels from 200($k$) to 200(m+k−1). By way of example, the ultrasound pulse transmitted in the first transmit is referred to as the first transmit pulse.

Figure 4A:
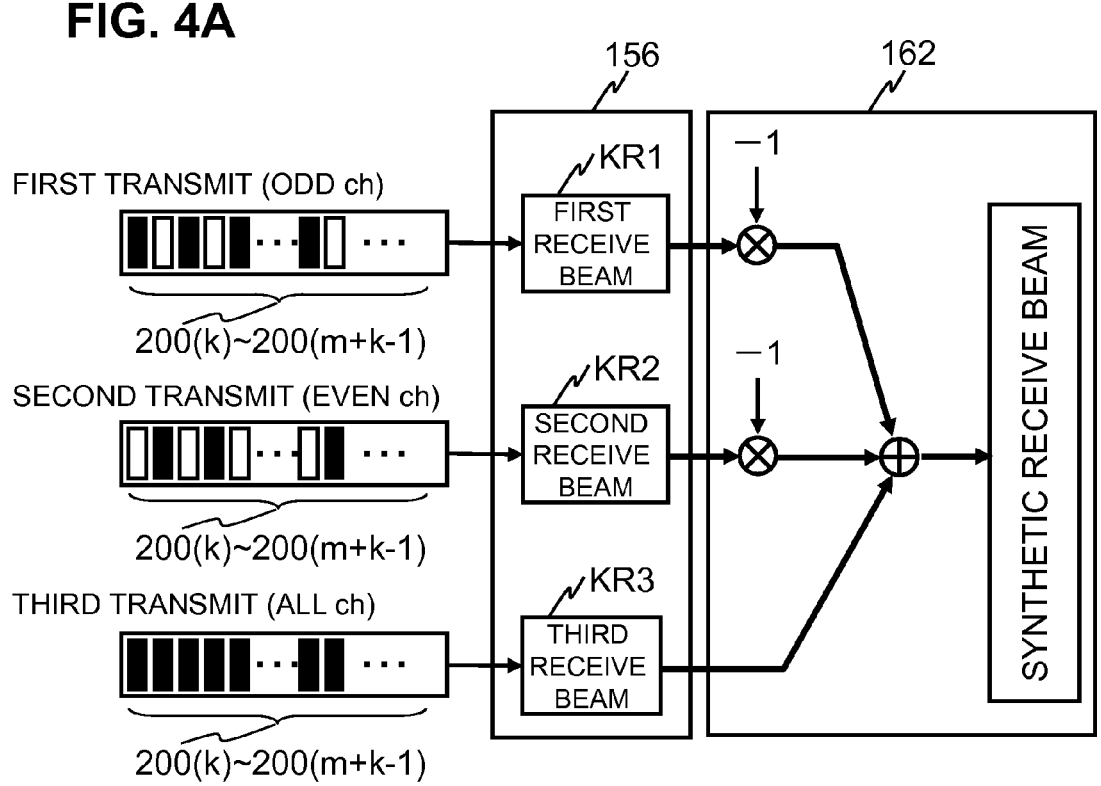
FIG. 4A illustrates the amplitude modulation method using the conventional transmit aperture.
Figure 4B:
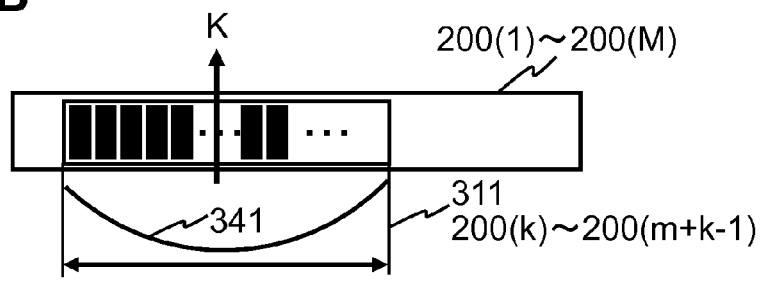
FIG. 4B illustrates the transmit apodization and the transmit focus delays of the amplitude modulation method using the conventional transmit aperture.

As illustrated in FIG. 4A, reflected waves (echo signals) from the first transmit pulse transmitted to the test subject are received, assuming the transmit and receive aperture 311 as the receive aperture. Then, the receive beamformer 156 forms the first receive beam KR1 therefrom, and it is stored in the memory 161. It is to be noted that the receive beamformer 156 forms the first receive beam. KR1, by giving the receive focus delays 341 to a group of the echo signals and summing those signals. As shown in FIG. 4B, the receive focus delays 341 is set to the raster K that is positioned at the center of the transmit and receive aperture 311.

In the transmit of the second time (the second transmit), it is controlled in such a manner that only the even channels (even ch) out of the channels from 200($k$) to 200(m+k−1) are excited. In other words, it is controlled so that the ultrasound pulses are transmitted only from the even channels. The reflected waves (echo signals) from the second transmit are received, assuming the transmit and receive aperture 311 as the receive aperture. Then, the receive beamformer 156 forms the second receive beam KR2 therefrom, and it is stored in the memory 161. It is to be noted that the receive beamformer 156 forms the second receive beam KR2, by giving the receive focus delays 341 to the group of the echo signals and summing those signals.

In the transmit of the third time (the third transmit), it is controlled in such a manner that all the channels of the channels from 200($k$) to 200(m+k−1) are excited. In other words, it is controlled so that the ultrasound pulses are transmitted from all the channels. The reflected waves (echo signals) from the third transmit are received, assuming the transmit and receive aperture 311 as the receive aperture. Then, the receive beamformer 156 forms the third receive beam KR3 therefrom, and it is stored in the memory 161. It is to be noted that the receive beamformer 156 forms the third receive beam KR3, by giving the receive focus delays 341 to the group of the echo signals and summing those signals.

Then, the signal processor 162 subtracts the summation of the first receive beam KR1 and the second receive beam KR2 from the third receive beam. KR3, thereby removing the fundamental wave component and extracting only the nonlinear component, and then a synthetic receive beam K at the position of the raster K is obtained.

As described above, in the amplitude modulation method using the conventional transmit sound field, in the transmits from the first transmit to the third transmit, the transmit apodization is set in such a manner that the transmit apodization of the third transmit corresponds to the synthesis of the transmit apodizations of the first transmit and the second transmit, and any of the transmit focus delays become equal. With this configuration, when the linear transmit sound field in the first transmit and the linear transmit sound field in the second transmit are synthesized, the synthetic acoustic field becomes equal to the linear acoustic field in the third transmit.

On the other hand, the first, the second, and the third transmit pulses that propagate through the test subject may cause waveform distortion, by the acoustic nonlinearity of the test subject, along with the propagation. In other words, the transmit pulses propagate through the test subject, with generating harmonics and low-frequency harmonics. Therefore, the first, the second, and the third receive beams stored in the memory 161 contain reflection echo components of the harmonics and low-frequency harmonics components.

Those harmonics and low-frequency harmonics have the magnitude being proportional to approximately the square of the sound pressure P of the transmitted fundamental wave pulse. Therefore, the sidelobe level of the harmonics or the low-frequency harmonics becomes smaller than the sidelobe level of the fundamental wave pulse. In addition, the harmonics and the low-frequency harmonics occur in a broadband. Therefore, an image obtained by imaging, using only the components of harmonics and low-frequency harmonics, is more excellent in contrast resolution and spatial resolution, than the image obtained by imaging, using the fundamental wave pulse component.

As described above, in the first transmit and in the second transmit, a transmit area becomes half of the area when the third transmit is performed. Therefore, when an identical voltage waveform is applied in every transmit to the channels 200 that are excited in the transmits from the first to the third, the sound pressure of the fundamental wave pulse in each of the first transmit and in the second transmit becomes half of the sound pressure of the fundamental wave pulse in the third transmit. In other words, when the sound pressure of the fundamental wave pulse in the third transmit is assumed as P, the sound pressure of the fundamental wave pulses in each of the first and the second transmits becomes P/2.

The harmonics and the low-frequency harmonics are generated in proportion to approximately the square of the sound pressure of the fundamental wave pulse. In other words, the sound pressure on the transmit sound field side in each of the first transmit and the second transmit is $(P/2)+(P/2)^2$. Here, the first term represents a linear component, and the second term represents a nonlinear component. On the other hand, when the sound pressure on the transmit sound field side in the third transmit is expressed in a similar manner, it is $P+P^2$. Since the sound pressure amplitude of the reflected echo is extremely small, if it is assumed that the relations of sound pressure are maintained even after the reflection, such relations are also maintained among the echo signals of the first, the second, and the third transmits, and among the receive beams respectively generated from those echo signals. In other words, when the magnitude of the sound pressure in the third receive beam is assumed as $R+R^2$, the magnitude of the sound pressure in each of the first receive beam and the second receive beam is expressed as $(R/2)+(R/2)^2$.

Therefore, the sum of the first receive beam KR1 and the second receive beam KR2 is subtracted from the third receive beam KR3, and the synthetic receive beam K being obtained corresponds to the signals being extracted, made up of the nonlinear component of $R^2/2$.

In the PI method being widely used as a conventional harmonic imaging method, two-time transmits are performed using ultrasound pulses being inverse with each other. Therefore, if the transmit amplifier, or the like, included in the transmit circuit 152, has any voltage-dependent distortion characteristics, there is a possibility that a fundamental wave pulse component remains.

On the other hand, in the harmonic imaging method according to the amplitude modulation method that utilizes the aforementioned synthesis of transmit apertures, an identical voltage waveform is applied to the channels 200 that are excited in any of the first, the second, and the third transmit. Therefore, even when the transmit amplifier, or the like, includes voltage-dependent distortion characteristics, only the harmonic components are able to be extracted. However, in the aforementioned harmonic imaging method according to the amplitude modulation method utilizing the synthesis of transmit apertures, three-time or more transmits and receptions are necessary in order to obtain the receive beam for one scanning line (raster).

Figure 5:
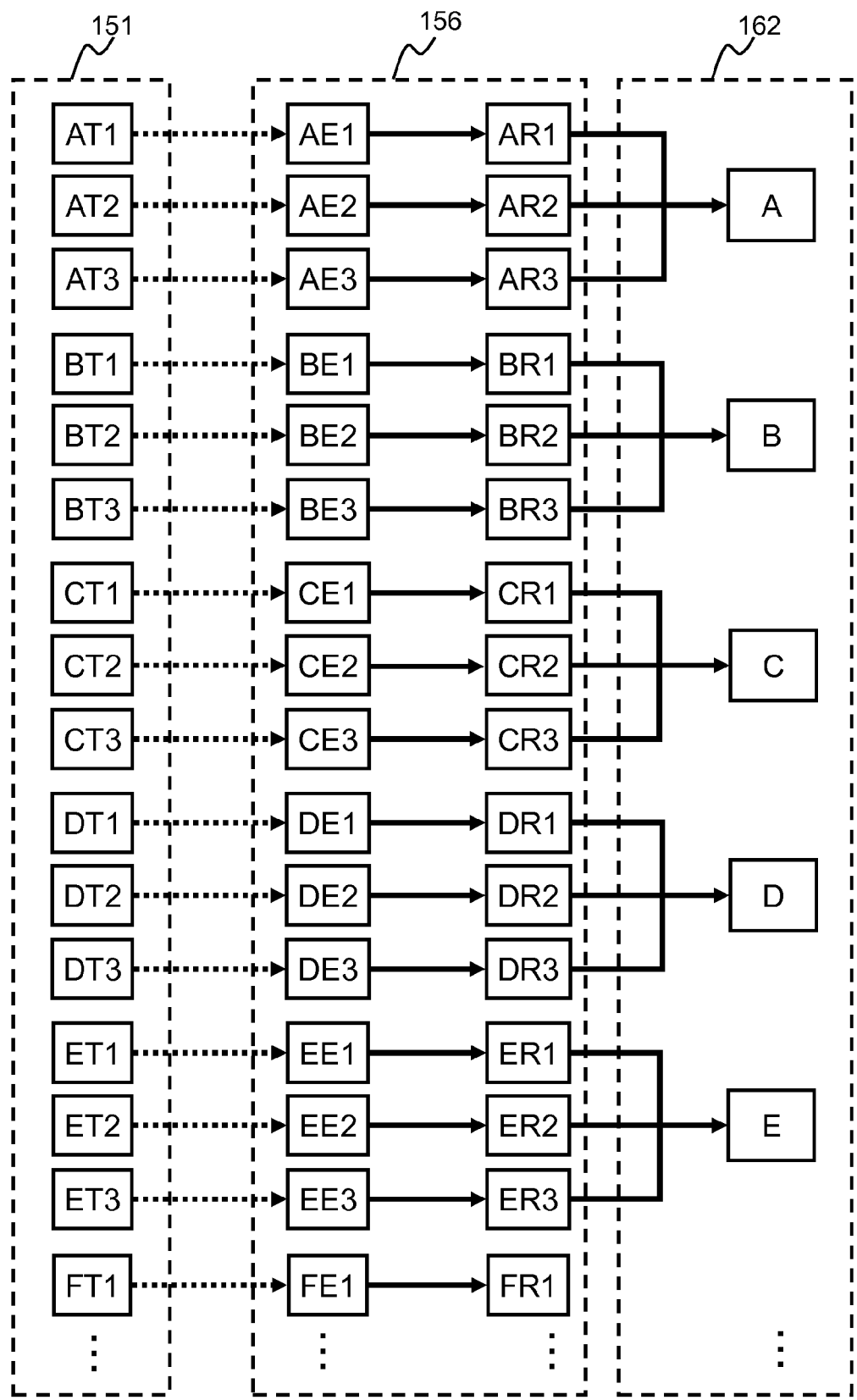
FIG. 5 illustrates the number of transmit/reception times of the amplitude modulation method using the conventional transmit aperture.

FIG. 5 illustrates a specific example indicating the number of transmit/reception times when the conventional method is employed. Here, an explanation will be made, taking an example that the transmit and receive aperture 310 is made to shift sequentially, and synthetic receive beams of the raster A, raster B, raster C, raster D, and raster E are generated, the rasters being adjacent to one another in this order.

As illustrated in the figure, in order to obtain the synthetic receive beam A of the raster A, three receive beams AR1, AR2, and AR3 are necessary, and those are obtained respectively from the three echo signals AE1, AE2, and AE3. In order to obtain those three echo signals AE1, AE2, and AE3, three-time transmits AT1, AT2, and AT3 are necessary for sending the transmit pulses.

Similarly, each of the following synthetic receive beams requires three-time transmits; the synthetic receive beam B of the raster B, the synthetic receive beam C of the raster C, the synthetic receive beam D of the raster D, and the synthetic receive beam E of the raster E.

As thus described, in order to obtain the synthetic receive beam for each of the rasters, three-time transmits and receptions are necessary, and therefore, the frame rate is deteriorated in comparison to the PI method that requires only two-time transmits and receptions. Therefore, there is a high possibility of causing somewhat slow movement in a moving image or occurrence of artifact due to body motion.

The ultrasound diagnostic apparatus 100 of the present embodiment implements the amplitude modulation method that improves such deterioration of frame rate and utilizes the synthesis of transmit apertures, that is, the harmonic imaging method achieving the frame rate approximately equivalent to that of the conventional PI method.

Next, the harmonic imaging method according to the amplitude modulation method utilizing the synthetic transmit aperture in the ultrasound diagnostic apparatus 100 of the present embodiment will be explained.

In the present embodiment, similar to the conventional method, in the first transmit, ultrasound pulses are transmitted from the odd channels in the transmit and receive aperture, in the second transmit, they are transmitted from the even channels in the transmit and receive aperture, and in the third transmit, they are transmitted from all the channels in the transmit and receive aperture. Then, on the basis of the echo signals obtained from the respective transmits, the first receive beam, the second receive beam, and the third receive beam are generated, and those beams are synthesized as described above, thereby forming the synthetic receive beam on a predetermined scanning line.

Figure 6:
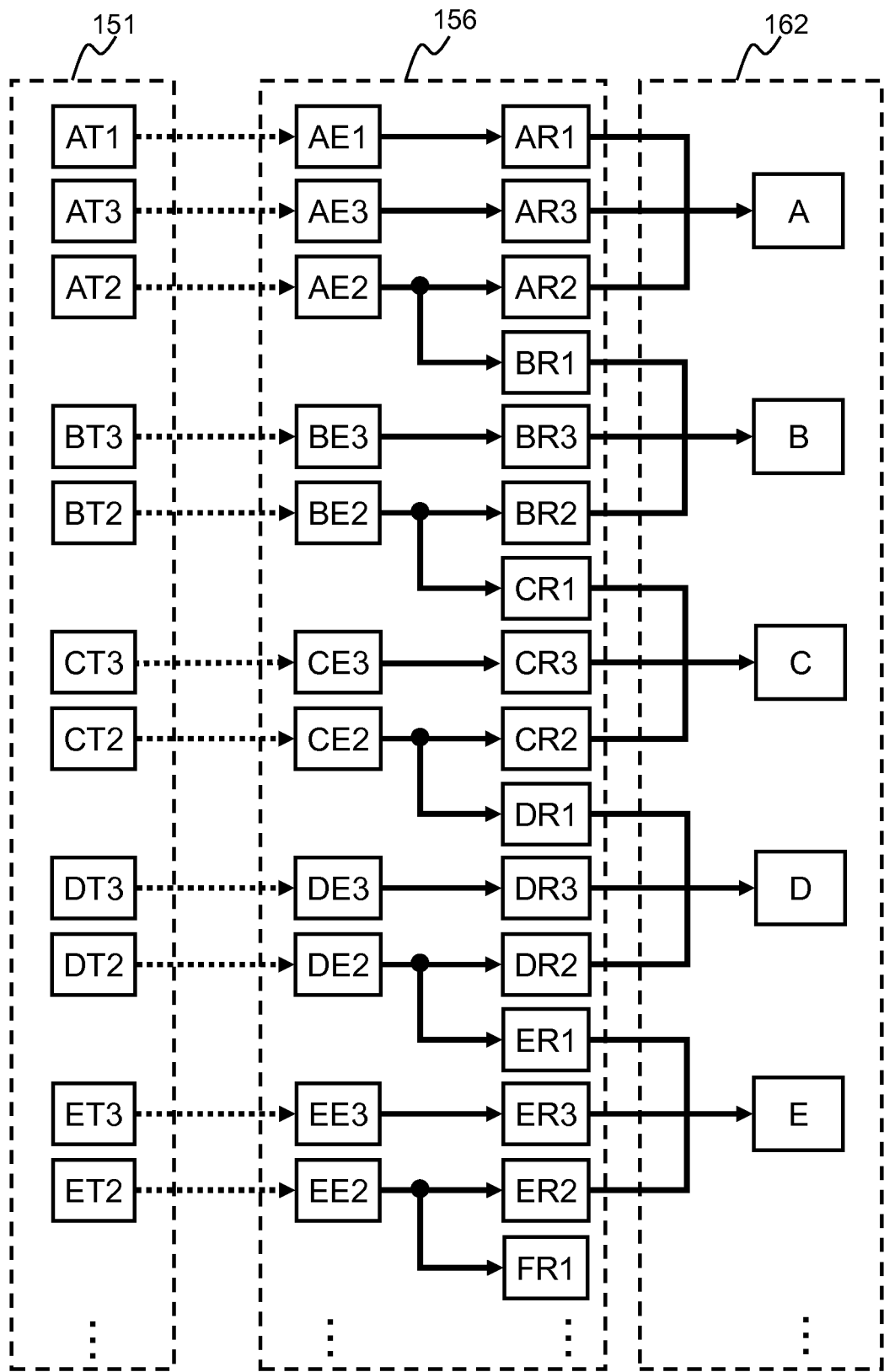
FIG. 6 illustrates the number of transmit/reception times of the first embodiment.

It is to be noted that in the present embodiment, the second transmit for each raster serves as the first transmit for the adjacent raster, and not only the second receive beam for the raster but also the first receive beam for the adjacent raster are generated, from the echo signal obtained by the second transmit. FIG. 6 illustrates a specific example of the number of transmit/reception times of the present embodiment. Similar to the case of FIG. 5, an explanation will be made, taking as an example that synthetic receive beams of the raster A, raster B, raster C, raster D, and raster E, are generated, the rasters being adjacent to one another in this order.

As illustrated, in order to obtain the first synthetic receive beam A of the raster A, three receive beams AR1, AR2, and AR3 are necessary, and those are obtained respectively from three echo signals AE1, AE2, and AE3. In order to obtain those three echo signals AE1, AE2, and AE3, three-time transmits AT1, AT2, and AT3 are required.

Similarly, in order to obtain the synthetic receive beam B of the raster B adjacent to the raster A, three receive beams BR1, BR2, and BR3 are required. The receive beam BR1 among the receive beams BR1, BR2, BR3 is generated from the echo signal AE2 that is obtained by the second transmit AT2 for the raster A. In other words, in the present embodiment, the second receive beam BR1 for the raster A and the first receive beam. AR1 for the raster B are obtained from the echo signal AE2 that is obtained by the second transmit AT2 for the raster A.

Therefore, in order to obtain the synthetic receive beam B of the raster B, three receive beams BR1, BR2, and BR3 are required, and those receive beams are obtained by the following transmits; the second transmit AT2 for the raster A, the second transmit BT2 for the raster B, and the third transmit BT3 for the raster B. In other words, only two-time transmits BT2 and BT3 for the raster B are sufficient.

Similarly, two-time transmits are sufficient for obtaining each of the synthetic receive beam C for the raster C, the synthetic receive beam D for the raster D, and the synthetic receive beam E for the raster E.

In the present embodiment, the aforementioned transmit and receive are implemented, by setting the transmit apodization and the transmit focus delays in the transmit beamformer 151, setting the receive apodization and the receive focus delays in the receive beamformer 156, and setting the transmit and receive aperture in the MUX 153. Hereinafter, details of the aforementioned settings to achieve this implementation will be explained. As to each raster, the number of channels used in the third transmit that uses all the channels is assumed as m. Here, it is assumed that m is an even number in the range between or equal to 1 and m.

Firstly, with reference to FIG. 7A, an explanation will be made regarding the setting of the transmit apodization and the transmit focus delays by the transmit beamformer 151, in the transmit for the first raster A. It is assumed that the channels from 200(1) to 200(m) are used in the transmit for the raster A.

Figure 7A:
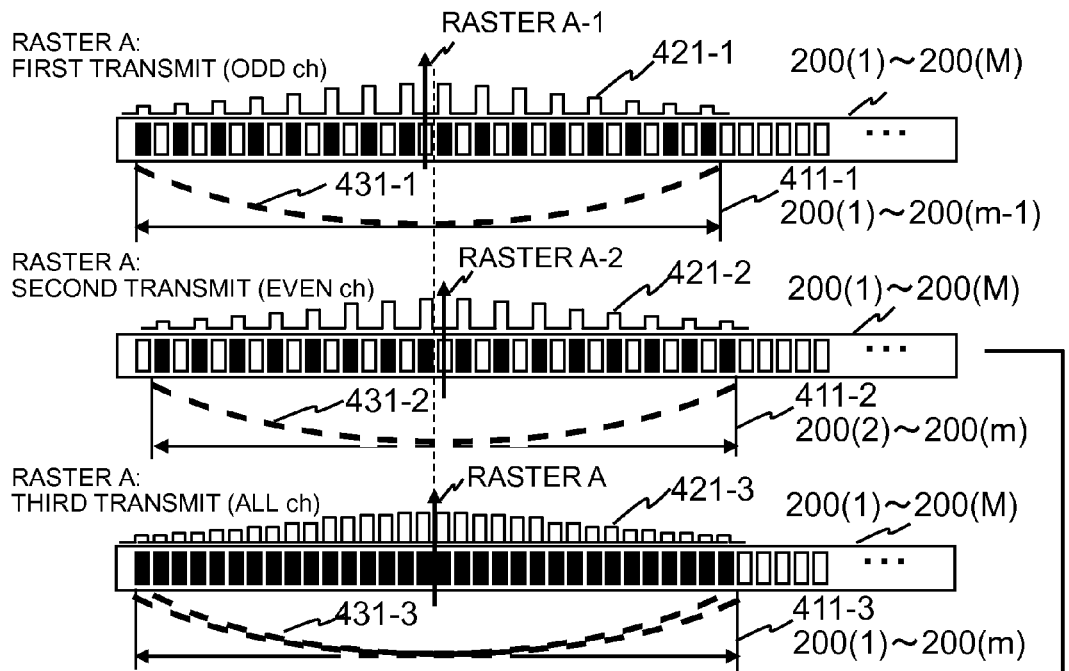
FIG. 7A illustrates the transmit apodization and the transmit focus delays in every transmit in the first embodiment.

As illustrated in the upper row of FIG. 7A, the transmit apodization 421-1 in the first transmit for the raster A is configured in such a manner that sound pressure is provided only to the odd channels out of the channels from 200(1) to 200(m). In other words, the transmit apodization 421-1 is set to the effective transmit aperture 411-1 that is specified as the range of the channels from 200(1) to 200(m−1). According to the transmit apodization 421-1, odd channels are selected as the transmit channels for transmitting the ultrasound pulses. In this case, the transmit focus delays 431-1 is formed for the raster A-1 at the center position of the effective transmit aperture 411-1.

As illustrated in the middle row of FIG. 7A, the transmit apodization 421-2 in the second transmit for the raster A is configured in such a manner that sound pressure is provided only to the even channels (even ch) out of the channels from 200(1) to 200(m). In other words, the transmit apodization 421-2 is set to the effective transmit aperture 411-2 that is specified as the range of the channels from 200(2) to 200(m). According to the transmit apodization 421-2, even channels are selected as the transmit channels for transmitting the ultrasound pulses. In this case, the transmit focus delays 431-2 is formed for the raster A-2 at the center position of the effective transmit aperture 411-2.

In the third transmit for the raster A, a synthesis of the transmit apodization 421-1 and the transmit apodization 421-2 is set as the transmit apodization 421-3. As illustrated in the lower row of FIG. 7A, the channels from 200(1) to 200(m) are configured in such a manner that sound pressure is provided to the odd and even channels in the channels from 200(1) to 200(m), i.e., to all the channels. In other words, the transmit apodization 421-3 is set to the effective transmit aperture 411-3 that is specified as the range of the channels from 200(1) to 200(m). According to the transmit apodization 421-3, all the channels are selected as the transmit channels for transmitting the ultrasound pulses.

In the third transmit for the raster A, a synthesis of the transmit focus delays 431-1 and the transmit focus delays 431-2 is set as the transmit focus delays 431-3. Here, as illustrated in the lower row of FIG. 7A, the transmit focus delays 431-1 for the raster A-1 and the transmit focus delays 431-2 for the raster A-2 are synthesized and formed for the raster A at the center position of the effective transmit aperture 411-3.

Next, with reference to FIG. 7B, an explanation will be made regarding the transmit for the raster B that is adjacent to the raster A. It is assumed that the channels from 200(2) to 200(m+1) are used in the transmit for the raster B.

Figure 7B:
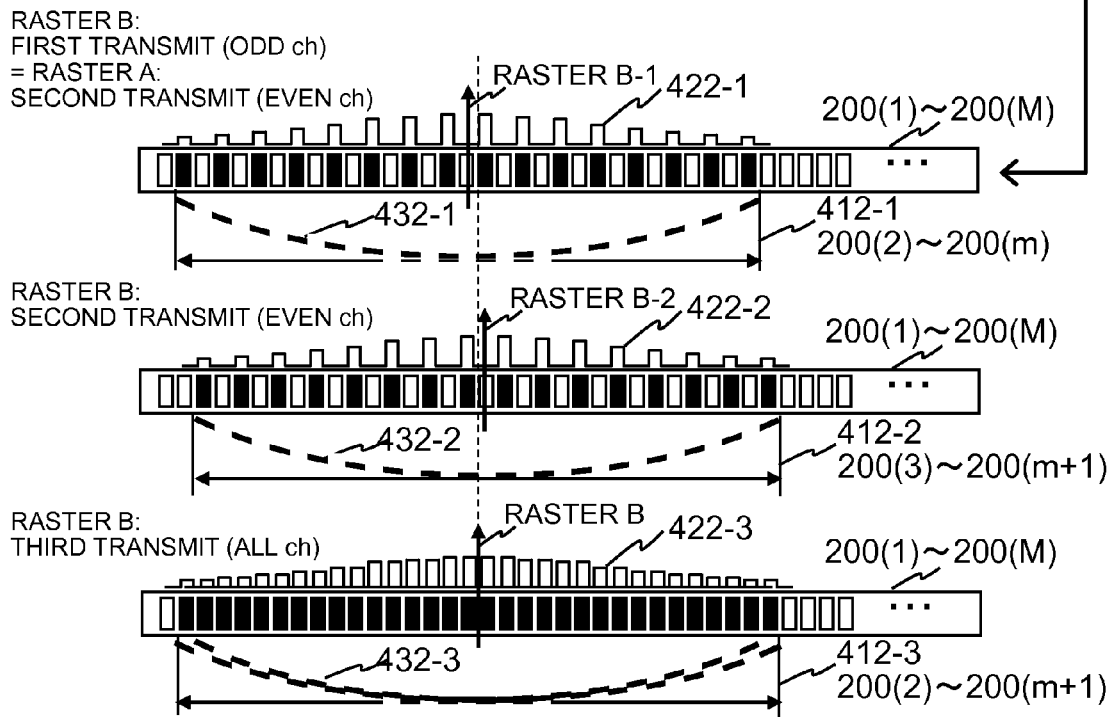
FIG. 7B illustrates the transmit apodization and the transmit focus delays in every transmit in the first embodiment.

As illustrated in the upper row of FIG. 7B, the transmit apodization 422-1 in the first transmit for the raster B is configured in such a manner that sound pressure is provided only to the odd channels out of the channels from 200(2) to 200 (m+1). Since the odd channels in the channels from 200(2) to 200(m+1) are the same as the even channels in the channels from 200(1) to 200(m), this transmit apodization 422-1 is made to coincide with the transmit apodization 421-2 of the second transmit for the raster A.

In the first transmit for the raster B, the transmit focus delays 432-1 is set to the center raster B-1 of the effective transmit aperture 412-1 that is specified as the range of the channels from 200(2) to 200(m). This effective transmit aperture 412-1 is the same as the effective transmit aperture 411-2 in the second transmit for the raster A. Therefore, this transmit focus delays 432-1 coincides with the transmit focus delays 431-2 of the second transmit for the raster A.

As described above, the transmit apodization 422-1 and the transmit focus delays 432-1 of the first transmit for the raster B are respectively equal to the transmit apodization 421-2 and the transmit focus delays 431-2 of the second transmit for the adjacent raster A. Therefore, in the present embodiment, it is not necessary to perform the first transmit for the raster B that is adjacent to the raster A, and the echo signal obtained by the second transmit for the raster A is utilized.

As illustrated in the middle row of FIG. 7B, the transmit apodization 422-2 in the second transmit for the raster B is configured in such a manner that sound pressure is provided only to the even channels out of the channels from 200(2) to 200(m+1). In other words, the transmit apodization 422-2 is set to the effective transmit aperture 412-2 that is specified as the range of the channels from 200(3) to 200(m+1). According to the transmit apodization 422-2, the even channels are selected as the transmit channels for transmitting the ultrasound pulses. In this case, the transmit focus delays 432-2 is formed on the raster B-2 at the center position of the effective transmit aperture 412-2.

Then, the echo signal obtained in the second transmit for the raster B is used for the raster C that is adjacent to the raster B.

In the third transmit for the raster B, a synthesis of the transmit apodization 422-1 and the transmit apodization 422-2 is set as the transmit apodization 422-3. As illustrated in the lower row of FIG. 7B, settings are configured in such a manner that sound pressure is provided to the odd and even channels in the channels from 200(2) to 200(m+1), i.e., all of the channels. In other words, the transmit apodization 422-3 is set to the effective transmit aperture 412-3 that is specified as the range of the channels from 200(2) to 200(m+1). According to the transmit apodization 422-3, all the channels are selected as the transmit channels for transmitting the ultrasound pulses.

In the third transmit for the raster B, a synthesis of the transmit focus delays 432-1 and the transmit focus delays 432-2 is set as the transmit focus delays 432-3. Here, as illustrated in the lower row of FIG. 7B, the transmit focus delays 432-1 for the raster B-1 and the transmit focus delays 432-2 for the raster B-2 are synthesized to form the transmit focus delays for the raster B at the center of the effective transmit aperture 412-3.

As thus described, in the present embodiment, the second transmit for a predetermined raster K (K is an integer at least 2) serves as the first transmit for the raster L that is adjacent to the raster K. The transmit beamformer 151 sets the transmit apodization and the transmit focus delays for each transmit in such a manner as enabling this sharing. In addition, the transmit apodization and the transmit focus delays of the third transmit, not shared, are configured so that they become equal respectively to the transmit apodization and the transmit focus delays that are obtained by synthesizing the first transmit and the second transmit.

With the configuration as described above, it is possible that the echo signals obtained by the second transmit for a predetermined raster are made to completely coincide with the echo signals that are supposed to be obtained by the first transmit for the adjacent raster.

Figure 8:
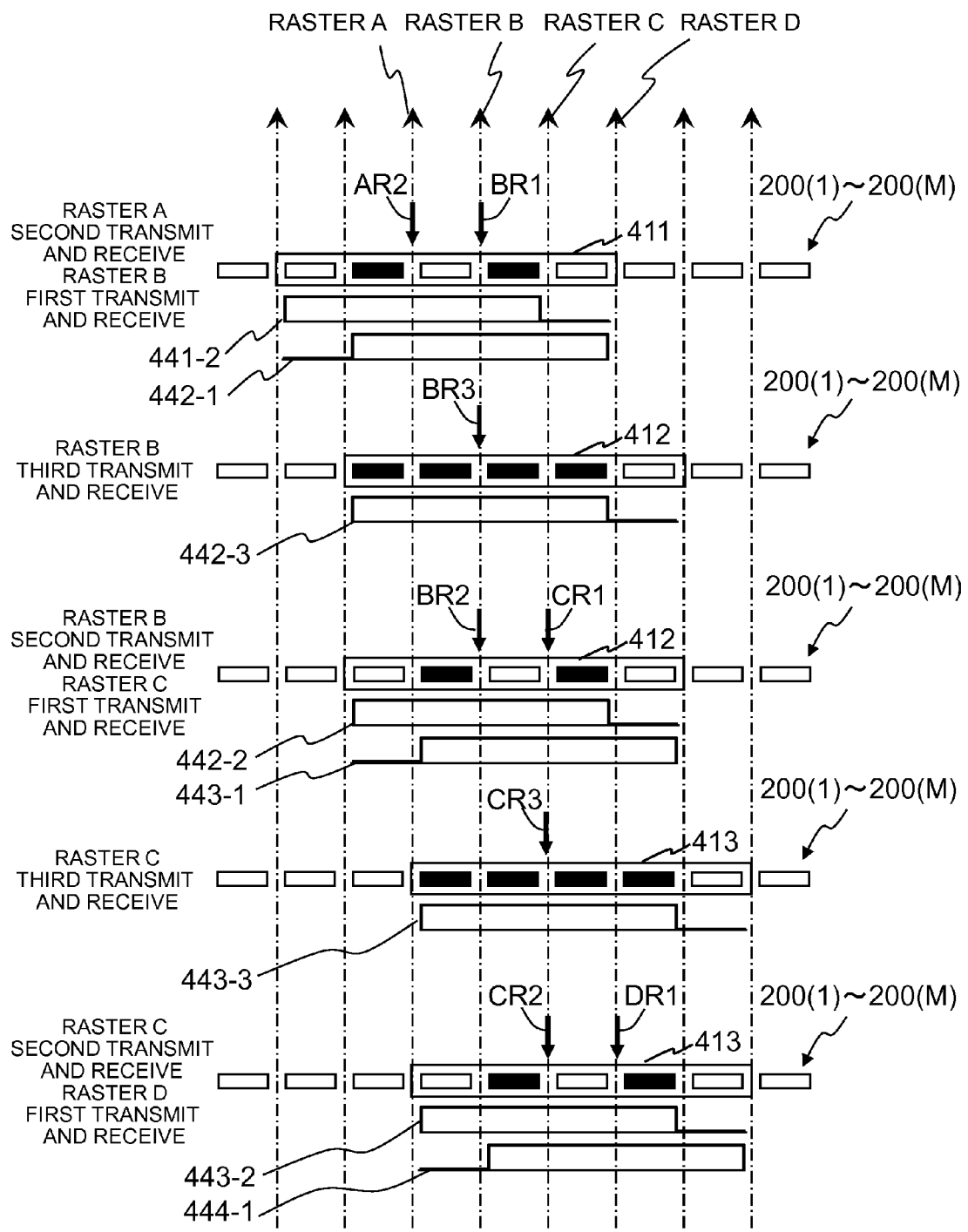
FIG. 8 illustrates the receive apodization in every receiving, and the transmit and receive aperture in every transmit and receive.

Next, with reference to FIG. 8, an explanation will be made regarding the receive apodization and the receive focus delays in receiving, being set by the receive beamformer 156 in the present embodiment.

As described above, the second transmit for an arbitrary raster K serves as the first transmit for the raster L that is adjacent to the raster K. Therefore, the receive beamformer 156 of the present embodiment forms receive beams respectively on the raster K and the raster L, from the echo signals obtained by this shared transmit. Hereinafter, an explanation will be made using a specific example as to the setting of the receive apodization in each receiving and the transmit and receive aperture in transmit and receive, in order to form the receive beams as described above.

Also in this explanation, the center position from the channel (1) to the channel (m) is assumed as the raster A, the center position from the channel (2) to the channel (m+1) is assumed as the raster B, and the center position from the channel (3) to the channel (m+2) is assumed as the raster C.

The second transmit for the raster A serves as the first transmit for the raster B that is adjacent to the raster A. Therefore, the receive beamformer 156 of the present embodiment sets the receive apodization in such a manner that when the echo signal is received from the second transmit for the raster A, the second receive beam AR2 and the first receive beam. BR1 are formed respectively on the raster A and the raster B, on the basis of the echo signal obtained from this transmit.

In order to form the second receive beam AR2 on the raster A, it is necessary for the receive beamformer 156 to sum a group of echo signals that are obtained by the channels from 200(1) to 200(m). On the other hand, in order to form the first receive beam BR1 on the raster B, it is necessary for the receive beamformer 156 to sum a group of echo signals that are obtained by the channels from 200(2) to 200(m+1).

Therefore, the receive beamformer 156 of the present embodiment sets two different receive apodizations. In other words, the receive apodization 441-2 is configured as the first receive apodization that selects the channels from 200(1) to 200(m) as the sum channels. Furthermore, the receive apodization 442-1 is configured as the second receive apodization that selects the channels from 200(2) to 200(m+1) as the sum channels.

The receive beamformer 156 sets the receive focus delays to be given respectively to the groups of echo signals obtained by the sum channels that are selected by the receive apodizations. Then, the receive beamformer 156 performs the addition process on the groups of echo signals extracted by the receive apodizations, respectively, while giving the receive focus delays being set, forms the second receive beam AR2 and the first receive beam BR1, and stores the beams in the memory 161.

The second transmit for the next raster B serves as the first transmit for the raster C that is adjacent to the raster B. Therefore, when the second transmit for the raster B is performed, the receive beamformer 156 of the present embodiment sets the receive apodization in such a manner that the second receive beam BR2 and the first receive beam CR1 are formed respectively on the raster B and the raster C from the echo signal that is obtained from the second transmit for the raster B.

In other words, in order to form the second receive beam BR2 on the raster B, the receive beamformer 156 sets the receive apodization 442-2 assuming the channels from 200(2) to 200(m+1) as the sum channels. Furthermore, in order to form the first receive beam CR1 on the raster C, the receive apodization 443-1 is set assuming the channels from 200(3) to 200(m+2) as the sum channels.

The receive beamformer 156 sets the receive focus delays given to the groups of echo signals that are obtained in the sum channels selected by the receive apodizations, respectively. Then, the receive beamformer 156 performs the addition process on the groups of echo signals extracted by the receive apodizations, respectively, while giving the receive focus delays being set, forms the second receive beam BR2 and the first receive beam CR1, and stores the beams in the memory 161.

It is to be noted that in the third transmit for the raster B, not shared as another transmit, the receive beamformer 156 sets the receive apodization 442-3 assuming the channels from 200(2) to 200(m+1) as the sum channels, in order to form the third receive beam BR3 for the raster B.

The receive beamformer 156 sets the receive focus delays to be given to the group of echo signals that are obtained in the sum channels selected by the receive apodization 442-3. Then, the receive beamformer 156 performs the addition process on the groups of echo signals extracted by the receive apodization, while giving the receive focus delays being set, forms the third receive beam BR3, and stores the beam in the memory 161.

The second transmit for the next raster C serves as the first transmit for the raster D that is adjacent to the raster C. Therefore, the receive beamformer 156 of the present embodiment sets the receive apodization in such a manner that the second receive beam CR2 and the first receive beam DR1 are formed respectively on the raster C and the raster D, from the echo signal obtained from the transmit for the raster C.

In other words, in order to form the second receive beam CR2 on the raster C, the receive beamformer 156 sets the receive apodization 443-2 assuming the channels from 200(3) to 200(m+2) as the sum channels. Furthermore, in order to form the first receive beam DR1 on the raster D, the receive apodization 444-1 is set, assuming the channels from 200(4) to 200(m+3) as the sum channels. In this case, the transmit and receive aperture 413 is set on the channels from 200(3) to 200(m+3) that contain both of beams.

The receive beamformer 156 further sets the receive focus delays to be given to the group of echo signals obtained in the sum channels selected by the receive apodizations, respectively. Then, the receive beamformer 156 performs the addition process on the groups of echo signals extracted by the receive apodizations, respectively, while giving the receive focus delays being set, forms the second receive beam CR2 and the first receive beam DR1, and stores the beams in the memory 161.

It is to be noted that in the third transmit for the raster C, not shared as another transmit, the receive beamformer 156 sets the receive apodization 443-3 assuming the channels from 200(2) to 200(m+1) as the sum channels, in order to form the third receive beam CR3 for the raster C.

The receive beamformer 156 sets the receive focus delays to be given to the group of echo signals that are obtained in the sum channels selected by the receive apodization 443-3. Then, the receive beamformer 156 performs the addition process on the groups of echo signals extracted by the receive apodization, while giving the receive focus delays being set, forms the third receive beam CR3, and stores the beam in the memory 161.

It is to be noted that in the present embodiment, the transmit also serving as the transmit for the adjacent raster forms the receive beams, respectively on two rasters being adjacent to each other. Therefore, at the time of receiving, the receive apodizations are set for both rasters respectively, covering the entire range of the transmit channels. By way of example, they are the receive apodizations 441-2 and 442-2 as shown in the top row of FIG. 8.

In order to achieve the aforementioned settings, in the present embodiment, the transmit and receive aperture is set in every transmit and receive, in such a manner as covering not only the range of all the transmit channels in the third transmit for one raster, but also the entire range of the transmit channels in the third transmit for the adjacent raster. By way of example, it may be the transmit and receive aperture 411 for the raster A in the second transmit, the transmit and receive aperture 412 for the raster B in the second and the third transmits, and the transmit and receive aperture 413 for the raster C in the second and the third transmits, and the like, as shown in FIG. 8. It is to be noted that the MUX 153 configures those settings as described above.

As thus described, the second transmit for the k-th raster K of the present embodiment serves as the first transmit for the raster L, that is the (k+1)th raster being adjacent to the raster K. Therefore, the receive beamformer 156 of the present embodiment sets the receive apodization from the echo signal obtained by this transmit in such a manner that the receive beams KR2 and LR1 are formed respectively on the raster K and the raster L.

In other words, in order to form the second receive beam KR2 on the raster K, the receive beamformer 156 sets the receive apodization, assuming the channels from 200($k$) to 200(m+k−1) as the sum channels. Furthermore, in order to form the first receive beam. LR1 on the raster L, the receive beamformer 156 sets the receive apodization, assuming the channels from 200(k+1) to 200(m+k) as the sum channels. In this case, the range of the channels from 200($k$) to 200(m+k) that includes both the receive beams is set as the transmit and receive aperture.

The receive beamformer 156 sets the receive focus delays, respectively, to be given to the group of echo signals that are obtained in the sum channels selected by the receive apodizations. Then, the receive beamformer 156 provides thus given receive delay, sums the group of signals in the sum channels, forms the second receive beam KR2 and the first receive beam LR1, and stores the beams in the memory 161.

It is to be noted that in the third transmit for the raster K, not shared as another transmit, the receive beamformer 156 sets the receive apodization, assuming the channels from 200($k$) to 200(m+k−1) as the sum channels, in order to form the third receive beam KR3 on the raster K. The transmit and receive aperture in the transmit and receive for this case is assumed as the channels from 200($k$) to 200(m+k).

On this occasion, the receive beamformer 156 further sets the receive focus delays along therewith. Then, the receive beamformer 156 performs the addition process on the groups of echo signals selected by the receive apodization, while giving the receive delay defined by the receive focus delays, forms the third receive beam. KR3, and stores the beam in the memory 161.

It is to be noted that the processing of the signal processor 162 is the same as the conventional manner. In other words, three different receive beams (the first receive beam, the second receive beam, and the third receive beam) formed on the respective rasters, via the three different apertures, are subjected to linear addition according to the aforementioned method, and a synthetic receive beam is obtained.

In the aforementioned present embodiment, the transmit apodization is formed as a rectangular weight, but the transmit apodization is not limited to this example. Byway of example, in order to reduce the side lobe of the transmit beam, it may be the hanning weight, hamming weight, or the like, which are defined for the channels being selected, according to the function of hanning window or the function of hamming window, or the hanning window with offset or the hamming window with offset, etc.

Furthermore, in order to reduce the side lobe of the receive beam, the aforementioned receive apodization may be defined for the channels being selected, according to the function of hanning window or the function of hamming window, or the hanning window with offset or the hamming window with offset, etc.

As described above, by using the aforementioned transmit method, the ultrasound diagnostic apparatus 100 of the present embodiment is allowed to acquire the receive beams according to the amplitude modulation method employing the two-time transmit and receive, being achieved by synthesizing the transmit apertures, except the time when the receive beams for the first scanning line (raster) are acquired. Therefore, compared to the conventional method that requires three-time transmit and receive for implementing the same operation, the number of transmit/reception times is reduced, and thereby enhancing the frame rate.

On the other hand, as illustrated in FIG. 7A, in the transmit for the raster A, in the first transmit that performs transmit from the odd channels, the range of the channels from 200(1) to 200(m−1) made up of the odd channels is assumed as the effective transmit aperture 411-1, and the transmit apodization 421-1 and the transmit focus delays 431-1 are set with respect to the raster A-1 being the center thereof, so as to perform the transmit. In the second transmit that performs transmit from the even channels, the range of the channels from 200(2) to 200($m$) made up of the even channels is assumed as the effective transmit aperture 411-2, and the transmit apodization 421-2 and the transmit focus delays 431-2 are set with respect to the raster A-2 being the center thereof, so as to perform the transmit.

In the third transmit that performs transmit from all the channels, the transmit apodization 421-3 obtained by synthesizing the transmit apodization 421-1 and the transmit apodization 421-2, and the transmit focus delays 431-3 obtained by synthesizing the transmit focus delays 431-1 and the transmit focus delays 431-2 are set, so as to perform the transmit.

In this situation, as illustrated in the bottom row of FIG. 7A, a transmit-delay level difference becomes larger between the adjacent channels, as coming closer to the edges of the effective transmit aperture (the range of the channels from 200(1) to 200($m$)) 411-3 in the third transmit incorporating all the channels. Next, a result of simulation will be described below, the simulation being conducted to find out the influence of deterioration in the transmit beam, caused by the transmit-delay level difference.

Conditions for the simulation were provided as the following; the center frequency of the transmit pulse was 6 MHz, the pitch of the channels was 0.2 mm, the number of channels was 64, focal distance was 30 mm, and the transmit apodization for the transmit from all the channels was rectangular weight. Properties of the acoustic medium were set as the following; the speed of sound was 1,530 m/s, the density was 1,000 kg/m$^3$, the absorption coefficient was 0.5 dB/cm/MHz, and the nonlinear parameter B/A was 7. Under these conditions, a beam profile was obtained indicating the transmit pulses and the harmonic component (synthetic receive beam) at the focal distance, for each of the amplitude modulation method according to the conventional transmit aperture synthesis, and the amplitude modulation method of the ultrasound diagnostic apparatus 100 according to the present embodiment. The KZK equation regarding the two-dimensional acoustic field was solved, and a nonlinear acoustic propagation analysis was performed, thereby obtaining the beam profile.

Figure 9:
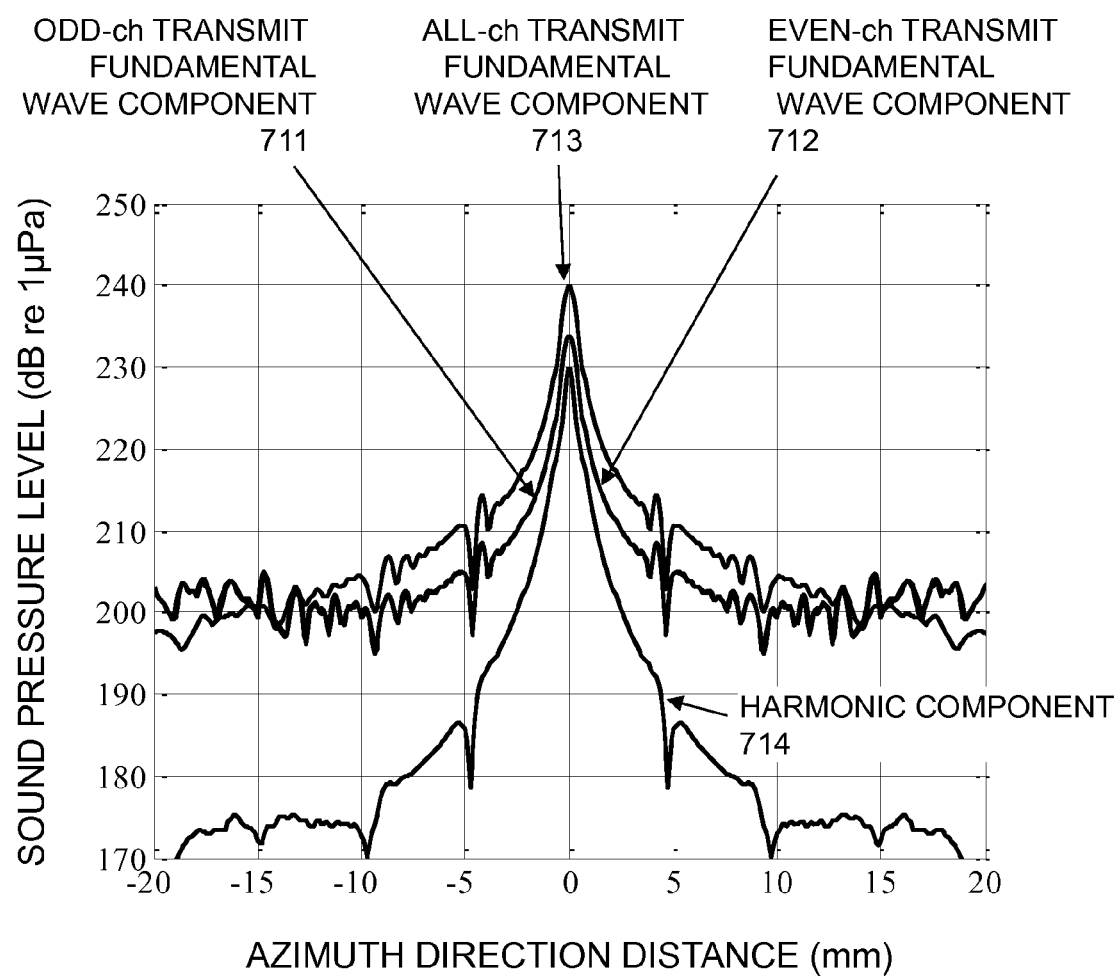
FIG. 9 illustrates a beam profile of the fundamental waves and the harmonic component of the amplitude modulation method using the conventional transmit aperture.

FIG. 9 illustrates the simulation result of the beam profiles (711, 712, 713, and 714) of the transmit pulses at the focal distance and each harmonic component being generated, according to the amplitude modulation method using the conventional synthesis of transmit apertures, as explained with reference to FIG. 3 to FIG. 5. Here, the vertical axis indicates the sound pressure level (dB re 1 μPa), and the horizontal axis indicates the distance in the azimuth direction (mm). It is to be noted here that the distance in the azimuth direction indicates the tangential direction at the center position of the targeted transmit and receive aperture 310.

In the amplitude modulation method using the conventional synthetic transmit aperture, the raster direction of the first transmit from the odd channels, the raster direction of the second transmit from the even channels, and the raster direction of the third transmit from all the channels are made to coincide, and transmit is made in such a manner as focusing on one point. Therefore, as illustrated in the figure, the beam profile 711 of the first transmit from the odd channels approximately coincides with the beam profile 712 of the second transmit from the even channels, and the beam profile 714 of the harmonic component being sharp with reduced side lobe is obtained.

Figure 10:
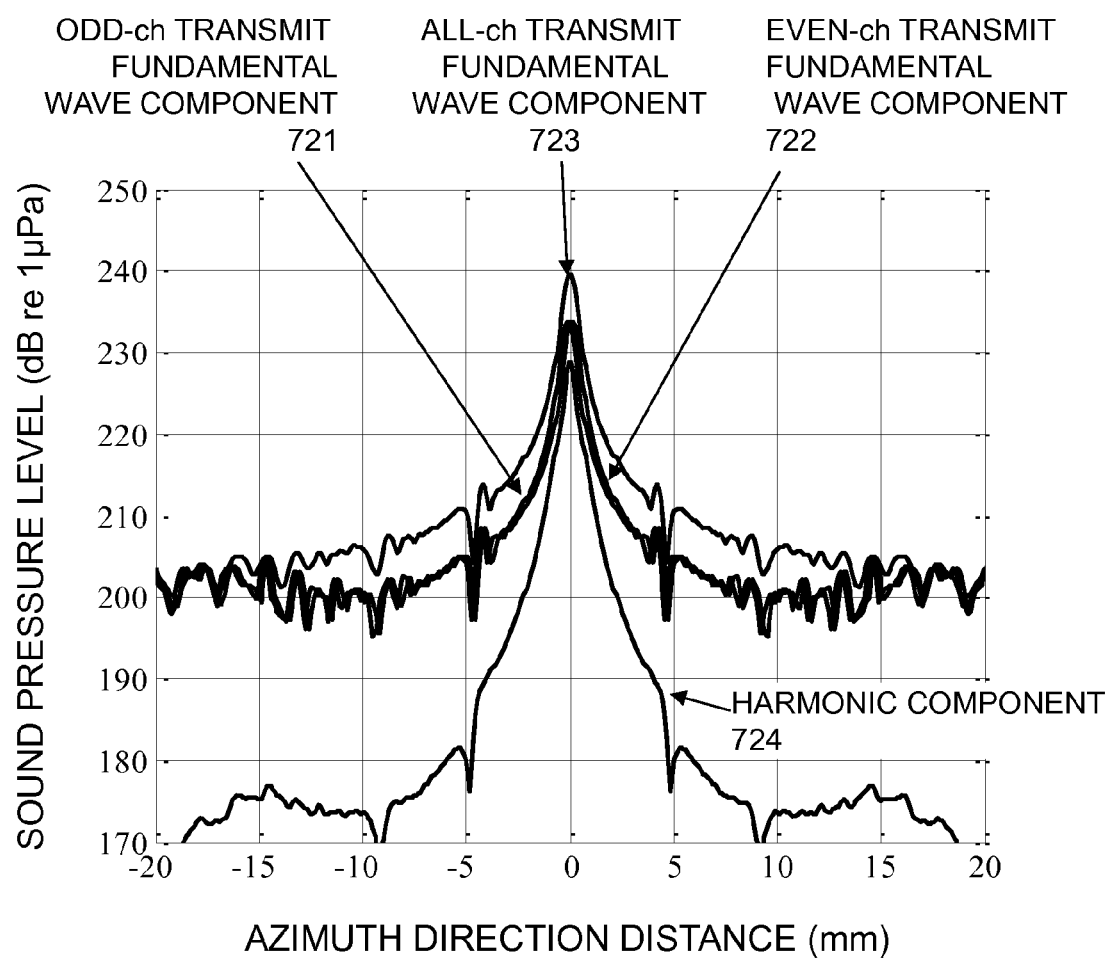
FIG. 10 illustrates the beam profile of the transmit sound field of the fundamental waves and the harmonic component according to the amplitude modulation method of the first embodiment.

FIG. 10 illustrates the simulation result of the beam profiles (721, 722, 723, and 724) of the transmit pulses at the focal distance and the generated harmonic component (synthetic receive beam), according to the amplitude modulation method using the synthetic transmit aperture in the ultrasound diagnostic apparatus 100 of the present embodiment. Here, the vertical axis indicates the sound pressure level (dB re 1 µPa), and the horizontal axis indicates the distance in the azimuth direction (mm).

In the amplitude modulation method using the synthetic transmit aperture of the present embodiment, the raster of the first transmit from the odd channels, and the raster of the second transmit from the even channels are located respectively on both sides of the raster of the third transmit from all the channels. Therefore, as illustrated in the figure, the beam profile 721 of the first transmit from the odd channels has the same shape as that of the beam profile 722 of the second transmit from the even channels, but slightly displaced in the azimuth direction.

When the beam profiles 713 and 723 of the third transmit from all the channels are compared, respectively shown in FIG. 9 and FIG. 10, the beam profile shape is almost the same. Similarly, the beam profile 724 of the harmonic component in FIG. 10 approximately coincides with the beam profile 714 of the harmonic component in FIG. 9, even though the peak sound pressure level is slightly lowered.

It is to be noted that as described above, in the analysis as shown in FIG. 9 and FIG. 10, the transmit apodization for the transmit from all the channels is configured as a rectangular weight, but it may be the banning weight.

As explained so far, according to the present embodiment, a part of the transmit and receive data for a predetermined raster may serve as apart of the transmit and receive data for the raster that is adjacent to the predetermined raster.

By way of example, when the amplitude modulation method is carried out according to the three-time transmit and receive, the transmit beamformer 151 sets the transmit apodizations, respectively, in such a manner that odd channels are selected out of the channels 200 in the first transmit to transmit the first transmit pulses for the scanning line A, and in the second transmit to transmit the second transmit pulses, even channels are selected out of the channels 200, as the transmit channels.

In the third transmit to transmit the third transmit pulses, the transmit apodization is configured in such a manner as synthesizing the transmit apodization set in the first transmit and the transmit apodization set in the second transmit. Similarly, as for the transmit focus delays, in the third transmit, the transmit focus delays is configured in such a manner as synthesizing the transmit focus delayset in the first transmit and the transmit focus delayset in the second transmit.

In this situation, the transmit apodization and the transmit focus delays in the second transmit are configured in such a manner that the second transmit also serves as the first transmit for the adjacent scanning line.

Furthermore, in the receive beamformer 156, as for the group of echo signals being received in response to the second transmit, some of the echo signals are selectable as a group to be summed for generating the receive beam for each scanning line. In other words, the receive apodization is set with respect to each scanning line, and generates the receive beam on each scanning line. Setting the receive apodization that differs from one scanning line to another, allows generation of the receive beams for the respective scanning lines, from one echo signal.

Furthermore, in the three-time transmits for each raster, the MUX 153 configures as the transmit and receive aperture, the channel range including the entire transmit channel range used by the third transmit for the first raster, and the entire transmit channel range used by the third transmit for the adjacent raster that shares the second transmit for the first raster.

Therefore, according to the present embodiment, when data for the adjacent scanning line is acquired, it is not necessary to transmit the first transmit pulse redundantly, but transmits of the second transmit pulse and the third transmit pulse are only required to obtain the data for the adjacent scanning line.

Consequently, when the synthetic receive beam is generated from the transmit and receive data, three-time transmit and receive are necessary only in the data acquisition for the first scanning line, and when data for other scanning lines is acquired, only two-time transmit and receive are sufficient.

In other words, according to the present embodiment, in the amplitude modulation method that requires more than one transmit and receive, a part of the transmit and receive necessary for obtaining the received signals of various scanning lines is able to be shared, and therefore, this may reduce the number of times of transmit/receive and enhance the frame rate. Therefore, this may eliminate somewhat slow movement in a moving image, allowing a smooth imaging without influence of body motion.

Furthermore, according to the present embodiment, it is possible to implement the amplitude modulation using the transmit aperture, in a few times of transmit. Since waveforms of the ultrasound pulses to be synthesized are generated in the form of the transmit sound field, not by electronic control, this enables transmit of a synthetic ultrasound pulse having a highly precise waveform. Even when there are voltage-dependent distortion and/or nonlinear characteristics in the transmit system of the ultrasound diagnostic apparatus incorporating the transmit amplifier, the ultrasound probe, and the like, it is possible to remove the fundamental wave component with a high degree of precision. This allows the THI to obtain an image with high contrast resolution and spatial resolution, and allows the CHI to obtain a contrast image with high CTR.

<Second Embodiment>

Next, the second embodiment to which the present invention is applied will be explained. In the first embodiment, each channel is used independently, and the transmit apertures of the odd channels and the even channels are synthesized. In the present embodiment, a channel block is formed using adjacent plural channels, and the transmit apertures are synthesized in units of channel blocks. In other words, the transmit aperture made up of the even channel blocks is synthesized with the transmit aperture made up of the odd channel blocks.

Hereinafter, in the present embodiment, an explanation will be made taking as an example that adjacent two channels form the channel block 210.

The ultrasound diagnostic apparatus of the present embodiment has basically the same configuration as the ultrasound diagnostic apparatus 100 of the first embodiment. As described above, in the present embodiment, the unit for synthesizing the transmit apertures is different. Therefore, in each transmit, setting of the transmit apodization and transmit focus delays by the transmit beamformer 151, setting of the receive apodization and the receive focus delays by the receive beamformer 156, setting of the transmit and receive aperture by the MUX 153, and a method for generating the receive parallel beams by the receive beamformer 156, are different from those of the first embodiment. Hereinafter, an explanation will be made regarding the present embodiment, focusing on the configuration different from the first embodiment.

Figure 11:
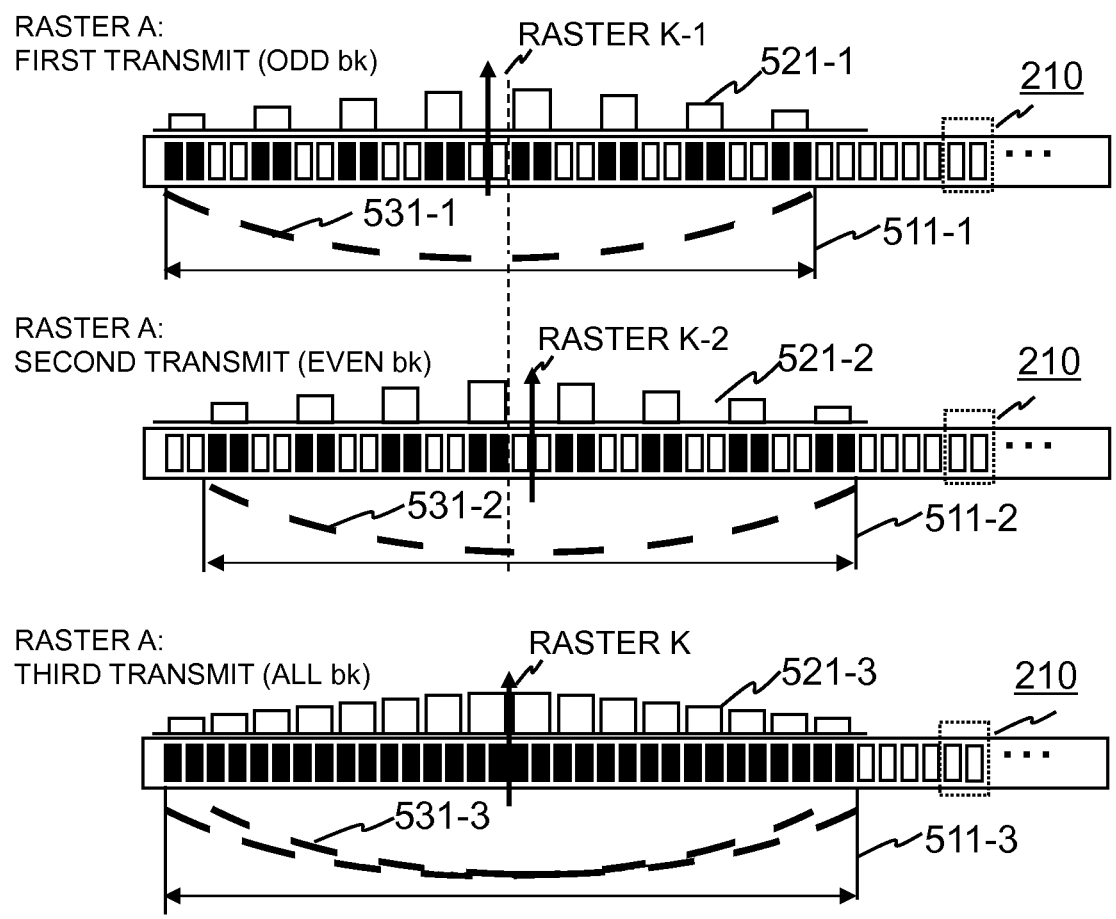
FIG. 11 illustrates the transmit apodization and the transmit focus delays in every transmit of the second embodiment.

Firstly, the transmit apodization and the transmit focus delays will be explained, which are set in every transmit by the transmit beamformer 151 of the present embodiment, so as to obtain the receive beams for one raster. As described above, in the present embodiment, the transmit apertures are synthesized in units of channel blocks. Therefore, the transmit apodization and the transmit focus delays are also configured in units of channel blocks. FIG. 11 illustrates the transmit apodization and the transmit focus delays that are set in transmit of the present embodiment. Here, an explanation will be made, taking as an example the transmit to obtain receive beams for a predetermined raster K.

Also in the present embodiment, the transmit beamformer 151 sets the transmit apodization and the transmit focus delays in every transmit, according to an instruction from the controller 130. The controller 130 holds in advance several types of settings regarding the transmit apodization and the transmit focus delays for each transmit, and outputs an instruction to the transmit beamformer 151 in response to the selection by a user.

In the first transmit for transmitting the first transmit pulse, the odd channel blocks (odd bk) 210 are assumed as the transmit channel blocks, and the transmit apodization 521-1 is set in such a manner that transmit pulses are transmitted only from those transmit channel blocks. In addition, it is assumed that the effective transmit aperture 511-1 corresponds to the channel blocks 210 on both edges and therebetween of the transmit channel blocks, and the transmit focus delays 531-1 is configured for the raster K-1 at the center of the effective transmit aperture.

In the second transmit for transmitting the second transmit pulse, the even channel blocks (even bk) 210 are assumed as the transmit channel blocks, and the transmit apodization 521-2 is set in such a manner that transmit pulses are transmitted only from those transmit channel blocks. It is assumed that the effective transmit aperture 511-2 corresponds to the channel blocks 210 on both edges and therebetween of the transmit channel blocks, and the transmit focus delays 531-2 is configured for the raster K-2 at the center of the effective transmit aperture.

In the third transmit for transmitting the third transmit pulse, the transmit apodization 521-1 set in the first transmit, and the transmit apodization 521-2 set in the second transmit are synthesized, thereby setting the transmit apodization 521-3. Similarly, as for the transmit focus delays, the transmit focus delays 531-1 set in the first transmit and the transmit focus delays 531-2 set in the second transmit are synthesized, thereby setting the transmit focus delays 531-3. Therefore, in this situation, the transmit focus delays 531-3 is set for the raster K at the center of the effective transmit aperture 511-3 that is obtained by synthesizing both the effective transmit apertures 511-1 and 511-2.

Then, the transmit apodization and the transmit focus delays in every transmit are configured in such a manner that the second transmit serves as the first transmit of the three transmits that are used for forming the adjacent raster.

Figure 12:
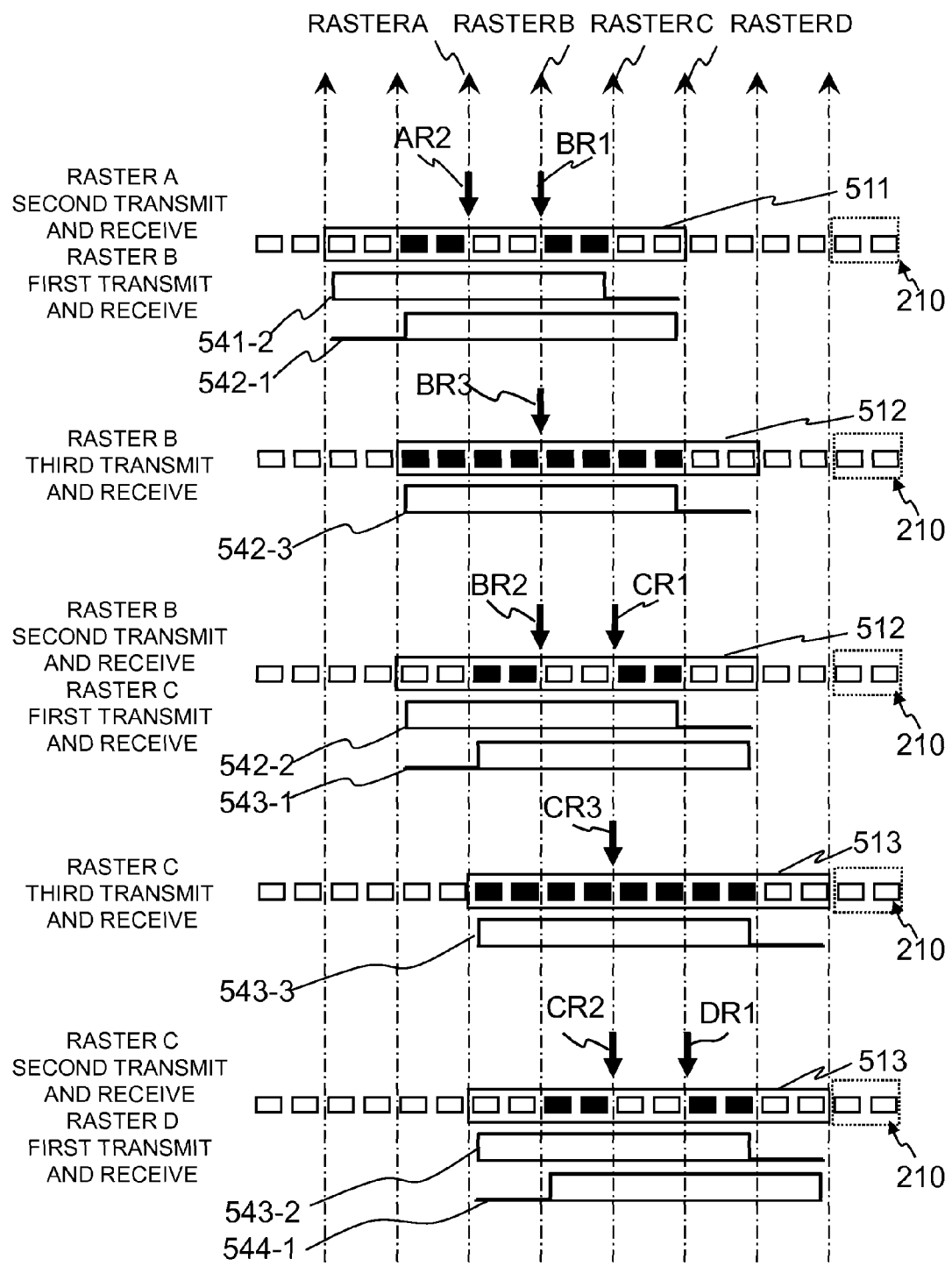
FIG. 12 illustrates the receive apodization in every receiving and the transmit and receive aperture in every transmit and receive of the second embodiment.

Next, setting of the receive apodization and the receive focus delays by the receive beamformer of the present embodiment will be explained. FIG. 12 illustrates the receive apodization and the receive focus delays being set in receiving time of the present embodiment. In this example here, the pitch is defined assuming the channel block 210 as one unit, and the synthetic receive beams are generated for the rasters in the order of the raster A, raster B, raster C, and raster D.

The receive beamformer 156 of the present embodiment, similar to the first embodiment, configures the receive apodization in such a manner that the echo signal received by the second transmit for a raster is used to form the receive beams respectively on the raster and the adjacent raster. Furthermore, the delay that is given to each of the echo signals in summation, is set as the receive focus delays. Then, a group of echo signals obtained by the sum channel blocks that are selected by thus determined receive apodization, are provided with the predetermined delays being defined by the receive focus delays, and along therewith, the group of echo signals are summed, so as to generate the receive beams with predetermined depths respectively on the predetermined raster and the raster adjacent thereto.

It is to be noted that in the third transmit, the receive beam is formed only on the predetermined raster.

By way of example, the second transmit for the raster A serves as the first transmit of the raster B. Therefore, in receiving the echo signal by the second transmit for the raster A, the receive beamformer 156 sets the receive apodizations 541-2 and 542-1. The receive beamformer 156 further sets the receive focus delays, and forms the second receive beam AR2 and the first receive beam BR1 respectively on the raster A and the raster B, from the echo signals of the sum channel blocks that are specified by the receive apodizations 541-2 and 542-1, respectively.

Similarly, the second transmit for the raster B serves as the first transmit for the raster C. Therefore, the receive beamformer 156 sets the receive apodization 542-2 for forming the second receive beam on the raster B, and the receive apodization 543-1 for forming the first receive beam on the raster C. Furthermore, the receive beamformer 156 forms the second receive beam BR2 and the first receive beam CR1 on the respective rasters, from the group of echo signals of the sum channel blocks that are specified by both receive apodizations, respectively, according to the receive focus delays being configured.

In the third transmit for the raster B, the receive beamformer 156 sets the receive apodization 542-3 for forming the third receive beam on the raster B, and forms the third receive beam BR3 on the raster B, from the group of echo signals thus obtained.

The second transmit for the raster C similarly serves as the first transmit for the raster D. Therefore, the receive beamformer 156 sets the receive apodization 543-2 for forming the second receive beam on the raster C, and the receive apodization 544-1 for forming the first receive beam on the raster D. Then, the receive beamformer 156 forms the second receive beam CR2 and the first receive beam DR1 on the respective rasters, from the group of echo signals of the sum channel blocks that are specified by both of the receive apodizations.

In the third transmit for the raster C, the receive beamformer 156 sets the receive apodization 543-3 for forming the third receive beam for the raster C, and forms the third receive beam CR3 on the raster C, from the group of echo signal being obtained.

As described above, since the receive beams are formed on the adjacent two rasters, also in the present embodiment, the range of the channel blocks 210 including all the transmit channel blocks 210 for both of the rasters is configured as the transmit and receive apertures 511, 512, and 513. In the present embodiment similarly, the MUX 153 controls the transmit and receive apertures.

In other words, when the synthetic receive beam of one raster is generated, if it is assumed that m channel blocks 210 are used in the transmit and receive for the raster K being the k-th raster from the end, the channel blocks 210 from 210(k) to 210 (m+k−1) are used. In the transmit and receive for the raster adjacent to the raster K, the channel blocks from 210 (k+1) to 210 (m+k) are used. Therefore, in the transmit and receive for the raster K, the MUX 153 configures the channel blocks from 210(k) to 210 (m+k) as the transmit and receive aperture.

Similar to the first embodiment, the signal processor 162 of the present embodiment subjects the three receive beams formed on the respective rasters to a linear addition according to the aforementioned method, and obtains a synthetic receive beam.

It is to be noted that with the configuration above, distance between the rasters being formed corresponds to a pitch of the number of channels constituting the channel block 210. In the aforementioned example, it corresponds to two-channel pitch, for instance. Therefore, the number of ultrasound wave transmits times for configuring one frame becomes smaller, and this may enhance the frame rate more. However, this may decrease the scanning line (raster) density, failing to obtain sufficient azimuth resolution, in some cases.

Figure 13:
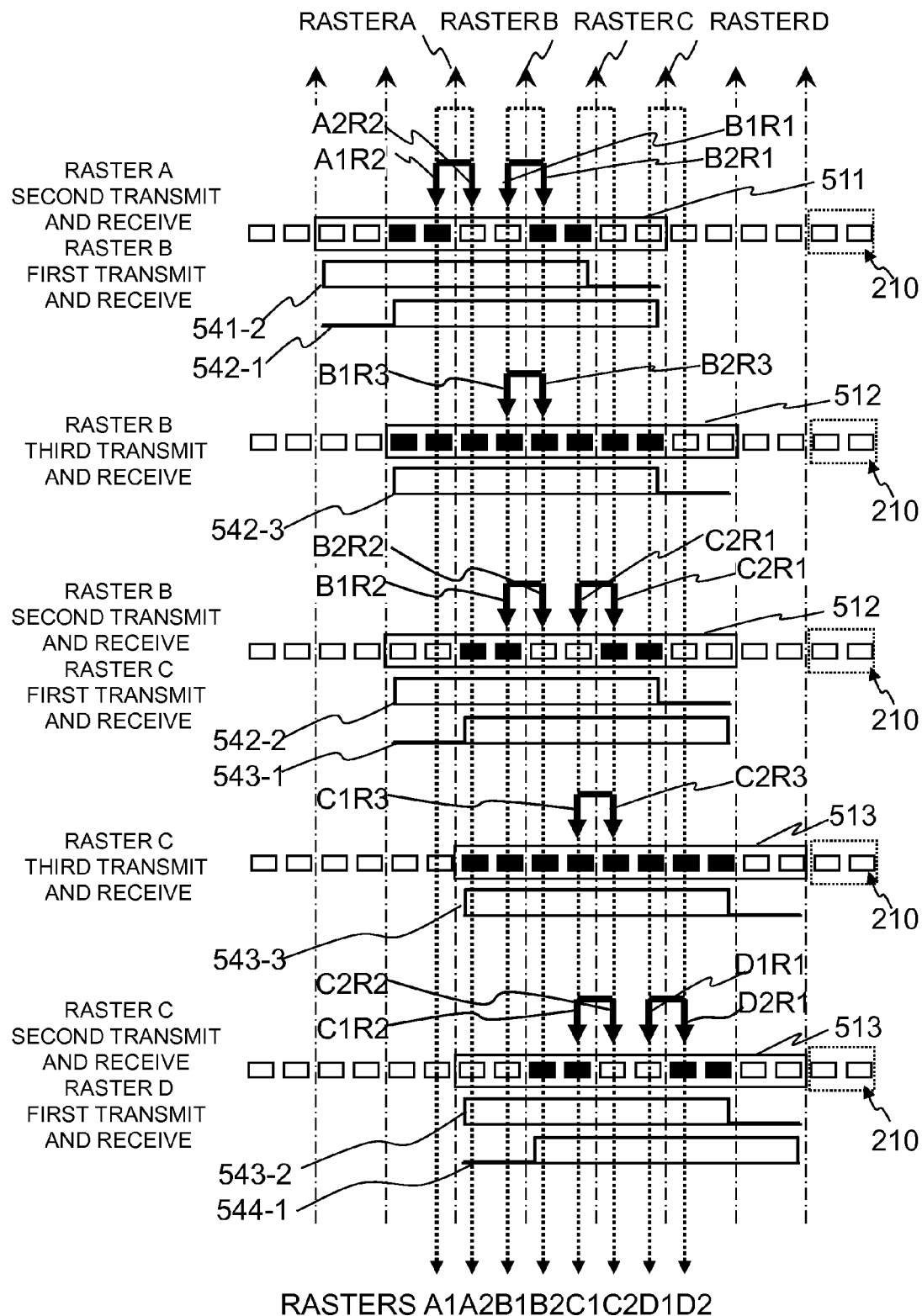
FIG. 13 illustrates the receive apodization in every receiving, the transmit and receive aperture in every transmit and receive, and the receive beams being formed in a modification example of the second embodiment.

In order to obtain the scanning line density being equal to that of the first embodiment, it is possible to configure such that two or more receive beams being shared among plural rasters are formed from one echo signal. The receive apodization and the receive focus delayset by the receive beamformer 156 in the case above will be explained. FIG. 13 illustrates the receive apodization and the receive focus delays of this modification example. It is assumed here that the synthetic receive beams are generated in the order of the raster A, raster B, raster C, and raster D, with a pitch of one channel block. An explanation will be made, taking as an example that the receive beams are generated on the four different rasters, from the echo signal received by the second transmit for each raster.

Similar to the case above, the receive beamformer 156 sets two receive apodizations in such a manner that the receive beams are able to be formed respectively on the two adjacent rasters, from the echo signal received by the second transmit for each raster. Then, the receive beamformer 156 provides two different receive focus delays to the group of echo signals obtained by the sum channel blocks that are specified by one receive apodization, thereby forming two different receive beams respectively on the two different rasters.

Also in the third transmit for each raster, the receive beamformer 156 provides two different receive focus delays to thus received echo signals, and forms the receive beams respectively on the two different rasters being the same as those in the second transmit. With reference to FIG. 13, the processing above will be explained, using a specific example.

In the second transmit for the raster A, the receive beamformer 156 sets the receive apodizations 541-2 and 542-1 on the echo signals being received. Those are the receive apodizations for forming the receive beams respectively on the rasters A and B. Then, the receive beamformer 156 provides two different delay time weights to the signals in the sum channel blocks that are specified by the receive apodization 541-2, so that the receive beams are formed on the raster A1 and the raster A2, and generates the second receive beams A1R2 and A2R2 on these rasters respectively. The receive beamformer 156 further provides two different focus delays to the signals in the sum channel blocks that are specified by the receive apodization 542-1, so that the receive beams are formed on the rasters B1 and B2, and generates the first receive beams B1R1 and B2R1 on these rasters, respectively.

In the third transmit for the raster B, the receive beamformer 156 sets the receive apodization 542-3 for forming the receive beam on the raster B. Then, the receive beamformer 156 provides two different delay time weights to the signals in the sum channel blocks that are specified by the receive apodization 542-3, so that the receive beams are formed on the rasters B1 and B2, and generates the third receive beams B1R3 and B2R3 on these rasters, respectively.

It is to be noted that the same is applied to other transmits. Similarly, the transmit and receive aperture is set by the MUX 153, assuming as its range, all the channel blocks used for the rasters sharing transmit.

In the modification example above, it is configured such that in the transmit being shared, the receive beamformer 156 forms the receive beams on two rasters respectively on both sides of the target raster, but the number of receive beams to be formed is not limited to this number. It is further possible to configure such that the receive beams are formed respectively on plural rasters, which places the target raster therebetween. In this situation, the receive beamformer 156 sets the receive apodization that defines the sum channels, scanning line by scanning line, and sets plural different receive focus delays to each of the receive apodizations, thereby forming the receive beams respectively on the plural rasters placing each scanning line therebetween.

It is further possible to configure such that the receive beamformer 156 sets four receive apodizations in the transmit being shared, and two receive apodizations in the third transmit not shared, and forms four and two receive beams, respectively.

In the present embodiment and its modification example, a configuration of one channel block made up of two channels has been explained as an example, but the number of channels constituting the channel block is not limited to this number. It may be three or more.

Figure 14:
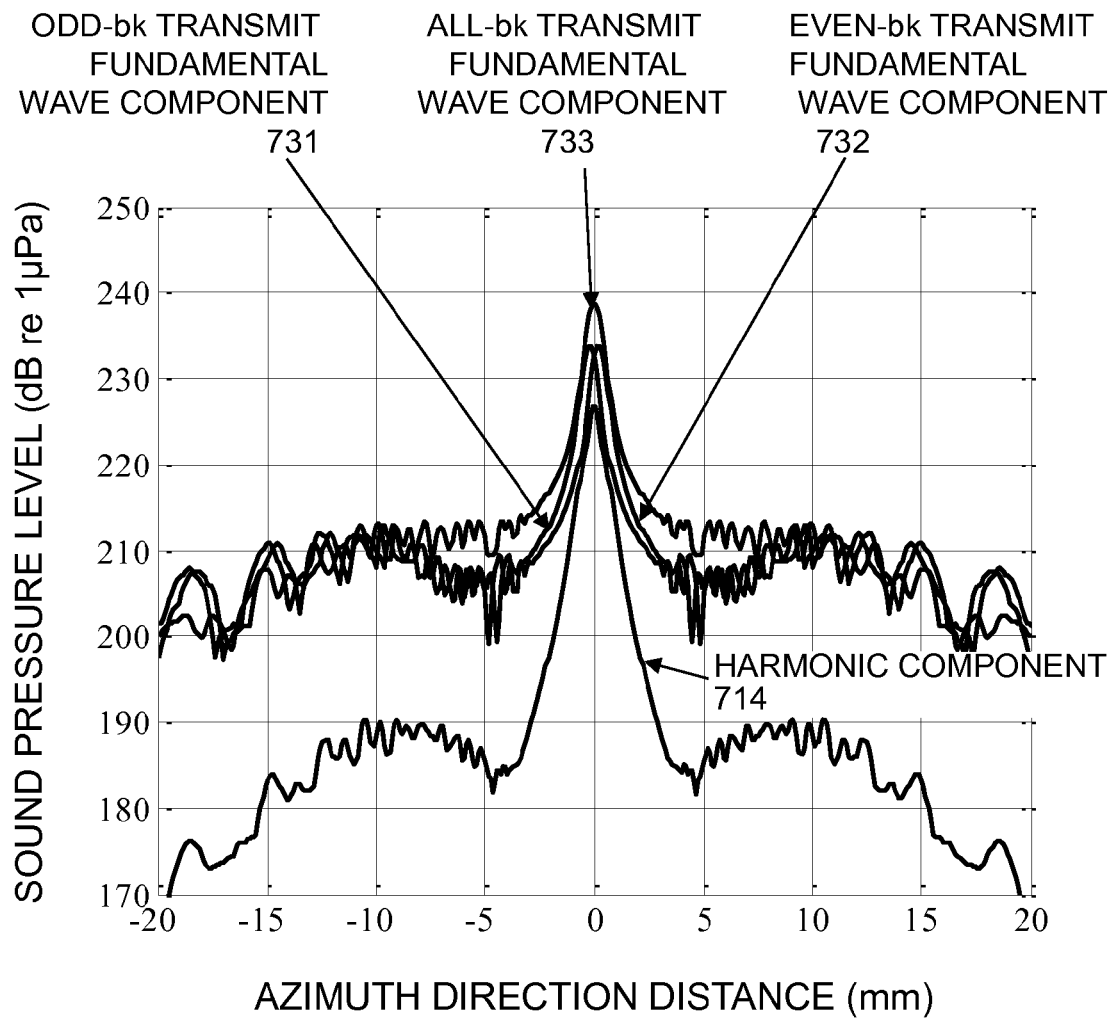
FIG. 14 illustrates the beam profile of the transmit sound field of the fundamental waves and the harmonic component according to the amplitude modulation method of the second embodiment.

FIG. 14 illustrates a simulation result of the beamprofiles (731, 732, 733, and 734) of the transmit pulses at focal distance and the harmonic component being generated, according to the amplitude modulation method synthesizing the transmit apertures in the modification example of the present embodiment. Here, the vertical axis indicates the sound pressure level (dB re 1 µPa), and the horizontal axis indicates the azimuth direction distance (mm).

As illustrated in the figure, the beam profile 731 of the odd channel blocks (odd bk) and the beam profile 732 of the even channel blocks (even bk) are obviously displaced in the azimuth direction. When the results in FIG. 9 and FIG. 10 are compared with this result, the beam profiles 731, 732, and 733 of the transmit sound field in FIG. 14 show the increase of the side lobe, resulting in that the sidelobe level of the harmonic component increases. On the main lobe, the resolution in the azimuth direction is deteriorated, and in addition, lowering of the peak sound pressure of the harmonic component is getting remarkable.

According to the result above, it is found that when the channel block including three or more channels per block is formed, increase of the side lobe and deterioration of the main lobe become remarkable. Therefore, it is desirable to form one channel block, using two channels at the maximum.

In the present analysis, as described above, the transmit apodization in the transmit from the all the channels is assumed as a rectangular weight, but it may be the hanning weight, or the like. Since the hanning weight is effective for reducing the side lobe, it is particularly effective in forming the channel block as in the case of the present modification example.

As described above, in the present embodiment, plural channels are treated as one block. Therefore, the distance between rasters corresponds to n-channel pitch (two-channel pitch is employed in the example above). Since this configuration reduces the number of ultrasound wave transmits, the frame rate is further improved.

In the present modification example, the first receive beams B1R1 and B2R1, for instance, are formed from the group of echo signals with the setting of receive apodization for one raster B. In other words, information at the position slightly displaced from the peak position in the azimuth direction is obtained, with respect to the main beam having a simple transmit peak in the azimuth direction as indicated by the harmonic component 734 in FIG. 14. This may cause lowering of a degree of homogeneity in the entire image.

Figure 1B:
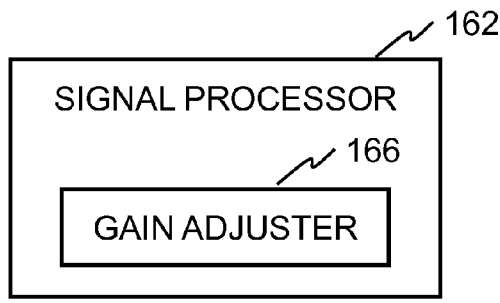
FIG. 1B is a functional block diagram illustrating a signal processor of the ultrasound diagnostic apparatus as a modification example of the second embodiment.

In the present embodiment, in order to solve this problem, as shown in FIG. 1B, the signal processor 162 may further be provided with a gain adjuster 166 configured to perform gain adjustment of the receive beam. The gain adjuster 166 performs digital arithmetic processing for performing gain adjustment of the receive beam. Gain adjustment according to the gain adjuster 166 allows the entire image to be homogenized.

It is to be noted here that in order to reduce the side lobe of the receive beam, the aforementioned receive apodization may be defined for the sum channels being selected, according to the function of hanning window or the function of hamming window, or the hanning window with offset or the hamming window with offset, etc.

As explained so far, in the present embodiment, the channel block is made up of the adjacent plural (two in the example above) channels, and it is configured as performing the first transmit via the odd channel blocks, and the second transmit via the even channel blocks. This configuration may extend the raster pitch. Consequently, the number of transmit/reception times per image frame is reduced, thereby improving the frame rate.

Furthermore, if it is configured such that the receive beams are formed on many different scanning lines from one echo signal, the number of transmits is reduced, while maintaining the scanning line density. Therefore, in order to obtain one synthetic receive beam from the received echo signals by three-time transmits, substantially two-time transmit and receive are sufficient, except for the first scanning line. Therefore, high-speed harmonic imaging is possible.

<Third Embodiment>

The third embodiment to which the present invention is applied will be explained. In any of the first and the second embodiments, one received signal is obtained via three-time transmitted and received data. In the present embodiment, the transmit aperture is further divided, and one received signal is generated, by using the transmitted and received data (received echoes) of four or more time.

The configuration of the ultrasound diagnostic apparatus 100 of the present embodiment is basically the same as the first embodiment. In the present embodiment, since the division number of the transmit aperture is different, the configurations of the transmit beamformer 151, the receive beamformer 156, and the signal processor 162 are also different. Hereinafter, the present embodiment will be explained, focusing on the configurations different from the first embodiment. In here, an explanation will be made taking as an example, the case where one received signal is generated by using four-time transmitted and received data (received echoes).

Also in the present embodiment, the transmit beamformer 151 sets the transmit apodization and the transmit focus delays for each transmit, and according to the settings, the transmit beams are transmitted from the plural channels 200 of the ultrasound probe 110. Further in the receive beamformer 156, the effective receive aperture, the receive apodization, and the receive focus delays are set, and the receive beams are obtained. In addition, the signal processor 162 generates a synthetic receive beam using the receive beams.

FIG. 15 illustrates the transmit and receive method of the present embodiment. Here, an explanation will be made taking the following case as an example; acquiring one synthetic receive beam from the receive beams, by four-time transmits in total, that is, three-time transmits and another one transmit that is performed via the transmit aperture obtained by synthesizing the transmit apertures of those three-time transmits above.

In the present embodiment, settings are configured such that the transmit apodization and the transmit focus delays in the third transmit for a predetermined raster A become equal to the transmit apodization and the transmit focus delays in each of the second transmit for the raster B being adjacent, and the first transmit for the raster C that is adjacent to the raster B. Also in the present embodiment, the transmit beamformer 151 configures those settings.

The transmit apodization and the transmit focus delays in the fourth transmit for the predetermined raster A is configured as the synthesis of the transmit apodization and the transmit focus delays obtained by synthesizing those in the first transmit, the second transmit, and the third transmit.

In addition, the receive apodization and the receive focus delays are configured as the following.

By way of example, for the echo signal obtained in the third transmit for the raster A, the receive apodization is set as the following; the receive apodization 641-3 for forming the receive beam AR3 on the raster A, the receive apodization 642-2 for forming receive beam BR2 on the raster B, and the receive apodization 643-1 for forming receive beam CR1 on the raster C. The receive beamformer 156 configures those settings. Then, the receive beamformer 156 forms each of the receive beam AR3, the receive beam BR2, and the receive beam CR1, and stores those beams in the memory 161.

Similarly, also for the echo signal obtained in the third transmit for raster B, three receive apodizations 642-3, 643-2, and 644-1 are set, and the receive beam BR3, the receive beam CR2, and the receive beam DR1 are formed respectively, and stored in the memory 161.

Similarly, also for the echo signal obtained in the third transmit for raster C, three receive apodizations 643-3, 644-2, and 645-1 are set, and the receive beam CR3, the receive beam DR2, and the receive beam ER1 are formed respectively, and stored in the memory 161.

Similarly, also for the echo signal obtained in the third transmit for raster D, three receive apodizations 644-3, 645-2, and 646-1 are set, and the receive beam DR3, the receive beam ER2, and the receive beam FR1 are formed respectively, and stored in the memory 161.

Similarly, also for the echo signal obtained in the third transmit for raster E, three receive apodizations 645-3, 646-2, and 647-1 are set, and the receive beam ER3, the receive beam FR2, and the receive beam GR1 are formed respectively, and stored in the memory 161.

In the fourth transmit for the raster C, for instance, which does not serve as the transmit for other rasters, the receive apodization 643-4 is set so that the receive beam is formed on the raster C, and the receive beam CR4 is formed. Similarly for the raster D and the raster E, the receive apodizations 644-4 and 645-4 are set, and the receive beams DR4 and ER4 are formed respectively.

The signal processor 162 synthesizes the receive beams obtained for the respective rasters, and forms a synthetic receive beam. As for the case of the raster C, for example, the summation of the receive beam CR1, the receive beam. CR2, and the receive beam. CR3 is subtracted from the receive beam CR4.

Furthermore, in each transmit, the MUX 153 sets the channels that are required for all the rasters that share the transmit, as the transmit and receive aperture.

As described above, according to the present embodiment, the first receive beam CR1 and the second receive beam CR2 for the raster C, for example, are obtained in the third transmit for the raster A and in the third transmit for the raster B, respectively. Therefore, the receive beam for the predetermined raster may be acquired by adding two more transmits and receptions.

As described above, when the division number of the transmit aperture is increased, it is possible to expect enhancement of signal intensity in the harmonic imaging according to the amplitude modulation method. Byway of example, in the example of FIG. 15 showing that the division number is three, when the sound pressure in the transmit from all the channels is assumed as P, the sound pressure via the first, the second, and the third partial aperture corresponds to P/3, respectively. Therefore, the received echo intensity is expressed as $(R/3)+(R/3)^2$, and when the transmits of three times are synthesized, it becomes equal to $R+(R^2/3)$. Therefore, the harmonic components being extracted becomes $(2R^2/3)$. That is, it is possible to obtain harmonic signals larger than $(R^2/2)$ that is obtained by the three-time transmit with the division number being two, as explained in the first and the second embodiments.

The number of transmit/reception times for obtaining one synthetic receive beam is not limited to the example above.

Also in the present embodiment, similar to the second embodiment, a block may be configured using plural channels, and the transmit aperture may be divided in units of blocks.

As described so far, the ultrasound diagnostic apparatus 100 of the present embodiment is configured to transmit ultrasound pulses to a test subject from the ultrasound probe provided with plural channels 200, and obtain an ultrasound image from echo signals being received, including the transmit beamformer 151 configured to set a transmit apodization that defines as the transmit channels, more than one transmit channel 200 for transmitting the ultrasound pulses, out of the plural channels, and the transmit focus delays that defines the delay time to be given to the ultrasound pulses transmitted from each of the transmit channels in every transmit, the receive beamformer 156 configured to generate a receive beam, from the echo signals received by the plural channels in every transmit, and the signal processor configured to generate a synthetic receive beam on one scanning line, by synthesizing n (n is an integer at least 3) receive beams and obtain an ultrasound image, where the n receive beams that generate the synthetic receive beam on one scanning line are generated respectively from the echo signals obtained by n different transmits, and at least one transmit out of the n different transmits is a shared transmit that serves as the transmit for a second scanning line that is different from the aforementioned one scanning line.

The transmit beamformer 151 may further be configured in such a manner that the transmit apodization and the transmit focus delays of one transmit (transmit having been synthesized), out of the n transmits, are equal to a synthesis of the transmit apodizations and a synthesis of the transmit focus delays of other (n−1) transmits (transmit to be synthesized). The receive beamformer 156 forms the receive beam on each of both the scanning lines, from the echo signals received from the shared transmit. Then, the receive beamformer 156 sets for every scanning line, the receive apodization defining the sum channels, and the receive focus delays defining the delay time to be given to the echo signals obtained via the sum channels, and forms the receive beam according to the receive apodization and the receive focus delays for each of the scanning lines. In this situation, the transmit apodization may be set in such a manner that the selected transmit channels are mutually exclusive, at the time of (n−1) transmits to be synthesized.

In addition, there is further provided the switch (MUX) 153 configured to determine the transmit and receive aperture corresponding to the channels 200 to be connected to the transmit beamformer 151 and the receive beamformer 156 for each transmit and receive, and the switch (MUX) 153 may determine as the transmit and receive aperture, all the transmit channels used by the transmit having been synthesized, for each of the two scanning lines that use the shared transmit as the transmit to be synthesized.

As described above, according to the present embodiment, in the amplitude modulation method that requires plural times of transmit and receive, it is possible to share a partial transmit and receive sequence, which is necessary for acquiring received signals on different scanning lines. Therefore, this enables enhancement of the frame rate, eliminating somewhat slow movement in a moving image, and allowing a smooth imaging without influence of body motion.

Even when there are voltage-dependent distortion and/or nonlinear characteristics in the transmit system of the ultrasound diagnostic apparatus incorporating the transmit amplifier, the ultrasound probe, and the like, it is possible to remove the fundamental wave component with a high degree of precision. This allows the THI to obtain an image with high contrast resolution and spatial resolution, and allows the CHI to obtain a contrast image with high CTR.

EXPLANATION OF REFERENCES

100: ultrasound diagnostic apparatus, 110: probe, 110: ultrasound probe, 120: controlled unit, 130: controller, 140:

UI, 151: transmit beamformer, 152: transmit circuit, 153: MUX, 154: T/R switch, 155: receive circuit, 156: receive beamformer, 161: memory, 162: signal processor, 163: detector, 164: DSC, 165: display unit, 166: gain adjuster, 200: channel, 210: channel block, 310: transmit and receive aperture, 311: transmit and receive aperture, 312: transmit and receive aperture, 321-1: transmit apodization of the first transmit, 321-2: transmit apodization of the second transmit, 321-3: transmit apodization of the third transmit, 322-1: transmit apodization of the first transmit, 322-2: transmit apodization of the second transmit, 322-3: transmit apodization of the third transmit, 331: transmit focus delays, 332: transmit focus delays, 411: transmit and receive aperture, 411-1: effective transmit aperture of the first transmit, 411-2: effective transmit aperture of the second transmit, 411-3: effective transmit aperture of the third transmit, 412: transmit and receive aperture, 412-1: effective transmit aperture of the first transmit, 412-2: effective transmit aperture of the second transmit, 412-3: effective transmit aperture of the third transmit, 413: transmit and receive aperture, 421-1: transmit apodization of the first transmit, 421-2: transmit apodization of the second transmit, 421-3: transmit apodization of the second transmit, 422-1: transmit apodization of the first transmit, 422-2: transmit apodization of the second transmit, 422-3: transmit apodization of the third transmit, 431-1: transmit focus delays of the first transmit, 431-2: transmit focus delays of the second transmit, 431-3: transmit focus delays of the third transmit, 432-1: transmit focus delays of the first transmit, 432-2: transmit focus delays of the second transmit, 432-3: transmit focus delays of the third transmit, 441-2: receive aperture of the second transmit and receive, 442-1: receive aperture of the first transmit and receive, 442-3: receive aperture of the third transmit and receive, 442-2: receive aperture of the second transmit and receive, 443-1: receive aperture of the first transmit and receive, 443-2: receive aperture of the second transmit and receive, 444-1: receive aperture of the first transmit and receive, 511: transmit and receive aperture, 511-1: effective transmit aperture of the first transmit, 511-2: effective transmit aperture of the second transmit, 511-3: effective transmit aperture of the third transmit, 512: transmit and receive aperture, 513: transmit and receive aperture, 521-1: transmit apodization of the first transmit, 521-2: transmit apodization of the second transmit, 521-3: transmit apodization of the third transmit, 531-1: transmit focus delays of the first transmit, 531-2: transmit focus delays of the second transmit, 531-3: transmit focus delays of the third transmit, 541-2: receive aperture of the second transmit and receive weight, 542-1: receive aperture of the first transmit and receive weight, 542-3: receive apodization of the third transmit and receive, 542-2: receive aperture of the second transmit and receive weight, 543-1: receive aperture of the first transmit and receive weight, 543-3: receive apodization of the third transmit and receive, 543-2: receive aperture of the second transmit and receive weight, 544-1: receive aperture of the first transmit and receive weight, 641-3: receive apodization of the third transmit and receive, 642-2: receive aperture of the second transmit and receive weight, 643-1: receive aperture of the first transmit and receive weight, 642-3: receive apodization of the third transmit and receive, 643-2: receive aperture of the second transmit and receive weight, 644-1: receive aperture of the first transmit and receive weight, 643-3: receive apodization of the third transmit and receive, 643-4: receive apodization of the fourth transmit and receive, 644-2: receive aperture of the second transmit and receive weight, 645-1: receive aperture of the first transmit and receive weight, 644-3: receive apodization of the third transmit and receive, 645-2: receive aperture of the second transmit and receive weight, 646-1: receive aperture of the first transmit and receive weight, 645-3: receive apodization of the third transmit and receive, 646-2: receive aperture of the second transmit and receive weight, 647-1: receive aperture of the first transmit and receive weight, 644-4: receive apodization of the fourth transmit and receive, 645-4: receive apodization of the fourth transmit and receive, 711: beam profile of the first transmit pulse, 712: beam profile of the second transmit pulse, 713: beam profile of the third transmit pulse, 714: beam profile of the harmonic component, 721: beam profile of the first transmit pulse, 722: beam profile of the second transmit pulse, 723: beam profile of the third transmit pulse, 724: beam profile of the harmonic component, 731: beam profile of the first transmit pulse, 732: beam profile of the second transmit pulse, 733: beam profile of the third transmit pulse, 734: beam profile of the harmonic component

What is claimed is:

1. An ultrasound diagnostic apparatus that transmits ultrasound pulses to a test subject, from an ultrasound probe provided with plural channels, and obtains an ultrasound image from echo signals being received, comprising, a transmit beamformer configured to set a transmit apodization that defines more than one transmit channels that transmit the ultrasound pulses, among the plural channels, and the transmit focus delays that defines delay time to be given to the ultrasound pulses transmitted from each of the transmit channels in every transmit, a receive beamformer configured to generate a receive beam, from the echo signals received by the plural channels in every transmit, and a signal processor configured to generate a synthetic receive beam on one scanning line, by synthesizing n receive beams and obtain an ultrasound image, wherein n is an integer at least 3 or more, the n receive beams that generate the synthetic receive beam on the one scanning line are generated respectively from the echo signals obtained by n different transmits, at least one out of the n different transmits is a shared transmit that serves as the transmit for another scanning line that is different from the one scanning line, and wherein the transmit beamformer configures the transmit apodization and the transmit focus delays of one transmit having been synthesized, out of the n different transmits, in such a manner as being equal to a synthesis of the transmit apodizations and a synthesis of the transmit focus delays of n−1 transmits to be synthesized.

2. The ultrasound diagnostic apparatus according to claim 1, wherein, the receive beamformer forms the receive beam on each of both the scanning lines, from the echo signals received by the shared transmit.

3. The ultrasound diagnostic apparatus according to claim 2, wherein, the receive beamformer configures a receive apodization defining sum channels with respect to each scanning line, and a receive focus delays defining the delay time given to the echo signals obtained by the sum channels, and forms the receive beam according to the receive apodization and the receive focus delays for each of the scanning lines.

4. The ultrasound diagnostic apparatus according to claim 1, wherein,
the transmit apodization is configured in such a manner that the transmit channels being mutually exclusive are selected in the n−1 transmits to be synthesized.

5. The ultrasound diagnostic apparatus according to claim 4, wherein,
n represents 3.

6. The ultrasound diagnostic apparatus according to claim 5, wherein,
the transmit apodization is configured in such a manner that odd channels are selected as the transmit channels in one of the transmits to be synthesized.

7. The ultrasound diagnostic apparatus according to claim 1, wherein,
the plural channels being adjacent constitute a channel block, and the transmit apodization and the transmit focus delays are configured in units of channel blocks.

8. The ultrasound diagnostic apparatus according to claim 7, wherein,
the receive beamformer forms the receive beams respectively on plural scanning lines that place therebetween, each of the two scanning lines both using the shared transmit, from the echo signals received by the shared transmit.

9. The ultrasound diagnostic apparatus according to claim 8, wherein,
the receive beamformer configures the receive apodization defining sum channels for each scanning line, further configures plural different receive focus delays for each of the receive apodization, and forms with respect to the one scanning line, the receive beams respectively on the plural scanning lines that place the one scanning line therebetween.

10. The ultrasound diagnostic apparatus according to claim 1, comprising,
a switch configured to determine a transmit and receive aperture corresponding to channels connected to the transmit beam former and the receive beamformer in every transmit and receive, wherein,
the switch determines as the transmit and receive aperture, all the transmit channels used in the transmit having been synthesized, for each of the two scanning lines that use the shared transmit as the transmit to be synthesized.

11. The ultrasound diagnostic apparatus according to claim 1, wherein,
the signal processor comprises a gain adjuster configured to perform gain adjustment of the receive beams.

12. An ultrasound image acquisition method in an ultrasound diagnostic apparatus having an ultrasound probe provided with plural channels, comprising the steps of:
transmitting a transmit beam from the ultrasound probe, according to a transmit apodization defining more than one transmit channels for transmitting ultrasound pulses, among the plural channels, and a transmit focus delays defining delay time given to the ultrasound pulses transmitted from each of the transmit channels,
generating a receive beam from the echo signals received by the plural channels in response to the transmit beam,
synthesizing n receive beams to generate a synthetic receive beam on one scanning line, and obtaining an ultrasound image, wherein n is an integer at least 3 or more,
the n receive beams for generating the synthetic receive beam on one scanning line are generated from the echo signals obtained respectively from n different transmits,
at least one transmit out of the n different transmits is a shared transmit that serves as the transmit for another scanning line that is different from the one scanning line, and
configuring the transmit apodization and the transmit focus delays in such a manner that the transmit apodization and the transmit focus delays for one transmit out of the n different transmits, are equal to a synthesis of the transmit apodizations and a synthesis of the transmit focus delays for n−1 transmits.

* * * * *